United States Patent
Lee et al.

(10) Patent No.: US 10,004,764 B2
(45) Date of Patent: Jun. 26, 2018

(54) RED BLOOD CELL MEMBRANE-DERIVED MICROPARTICLES AND THEIR USE FOR THE TREATMENT OF LUNG DISEASE

(71) Applicant: University of Pittsburgh—Of the Commonwealth System of Higher Education, Pittsburgh, PA (US)

(72) Inventors: Janet S. Lee, Pittsburgh, PA (US); Timothy E. Corcoran, Pittsburgh, PA (US); Valerian Kagan, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 0 days. days.

(21) Appl. No.: 15/034,700

(22) PCT Filed: Nov. 6, 2014

(86) PCT No.: PCT/US2014/064352
§ 371 (c)(1),
(2) Date: May 5, 2016

(87) PCT Pub. No.: WO2015/069897
PCT Pub. Date: May 14, 2015

(65) Prior Publication Data
US 2016/0263156 A1    Sep. 15, 2016

Related U.S. Application Data

(60) Provisional application No. 61/901,247, filed on Nov. 7, 2013.

(51) Int. Cl.
| | |
|---|---|
| A61K 9/127 | (2006.01) |
| A61K 35/18 | (2015.01) |
| A61K 9/00 | (2006.01) |
| A61K 9/14 | (2006.01) |
| A61K 35/12 | (2015.01) |

(52) U.S. Cl.
CPC ............ *A61K 35/18* (2013.01); *A61K 9/0075* (2013.01); *A61K 9/0078* (2013.01); *A61K 9/127* (2013.01); *A61K 9/14* (2013.01); *A61K 2035/124* (2013.01); *Y10S 977/773* (2013.01); *Y10S 977/906* (2013.01); *Y10S 977/907* (2013.01)

(58) Field of Classification Search
None
See application file for complete search history.

(56) References Cited

U.S. PATENT DOCUMENTS

| | | | | |
|---|---|---|---|---|
| 4,752,466 A | * | 6/1988 | Saferstein | A61K 9/12 424/45 |
| 6,294,153 B1 | * | 9/2001 | Modi | A61K 9/006 424/130.1 |
| 2005/0226916 A1 | * | 10/2005 | Cochrum | A61F 13/00034 424/445 |
| 2008/0069807 A1 | * | 3/2008 | Jy | A61K 35/18 424/93.72 |

FOREIGN PATENT DOCUMENTS

| | | | |
|---|---|---|---|
| WO | WO 2003/024419 | 3/2003 | |
| WO | WO 2006/062945 | 6/2006 | |
| WO | WO 2012/103512 | 8/2012 | |
| WO | WO-2012120131 A1 * | 9/2012 | ............. C07K 14/78 |

OTHER PUBLICATIONS

MD Smirnov, DA Ford, CT Esmon, NL Esmon. "The Effect of Membrane Composition on the Hemostatic Balance." Biochemistry, vol. 38, 1999, pp. 3591-3598.*
W Jy, ME Johansen, C Bidot Jr., LL Horstman, YS Ahn. "Red cell-derived microparticles (RMP) as haemostatic agent." Thrombosis and Haemostasis, vol. 110, 2013, pp. 751-760, published online Sep. 12, 2013.*
H Steckel, F Eskandar. "Factors affecting aerosol performance during nebulization with jet and ultrasonic nebulizers." European Journal of Pharmaceutical Sciences, vol. 19, 2003, pp. 443-455.*
O Rubin. "Erythrocytes Microparticles." University of Geneva, Masters Thesis, 2007, pp. 1-37.*
ME Greenberg, M Sun, R Zhang, M Febbraio, R Silverstein, SL Hazen. "Oxidized phosphatidylserine—CD36 interactions play an essential role in macrophage-dependent phagocytosis of apoptotic cells." Journal of Experimental Medicine, vol. 203 No. 12, 2006, pp. 2613-2625. (Year: 2006).*
Dodge et al., "The Preparation and Chemical Characteristics of Hemoglobin-Free Ghosts of Human Erythrocytes," *Arch. Biochem. Biophys.*, vol. 100:119-130, 1963.
Fabisiak et al., "Quantification of Selective Phosphatidylserine Oxidation During Apoptosis," *Molecular Toxicology Protocols*, Methods in Molecular Biology, vol. 1105:603-611, 2014.
Hu et al., "Erythrocyte membrane-camouflaged polymeric nanoparticles as a biomimetic delivery platform," *Proc Natl Acad Sci USA* 108(27):10980-10985, 2011.
Merkel et al., "Using mechanobiological mimicry of red blood cells to extend circulation times of hydrogel microparticles," *Proc Natl Acad Sci USA* 108(2):586-591, 2011.

(Continued)

*Primary Examiner* — Isaac Shomer
(74) *Attorney, Agent, or Firm* — Klarquist Sparkman, LLP

(57) ABSTRACT

Cell-based therapies show considerable potential as an immunomodulatory strategy for a variety of lung diseases, including chronic obstructive pulmonary disease (COPD), asthma, bronchiolitis, acute lung injury, lung allograft rejection (acute or chronic), pulmonary fibrosis. Described herein is the development of red blood cell membrane-derived microparticles (RBC MPs), which are depleted of hemoglobin (Hb) and express phosphatidylserine on their surface, for the treatment of lung disease. Administration of RBC MPs to the lung via inhalation promotes the production of immunoregulatory cytokines (such as IL-10), and reduces inflammation and injury in the lung.

15 Claims, 9 Drawing Sheets

(56) References Cited

OTHER PUBLICATIONS

Puddu et al., "The Involvement of Circulating Microparticles in Inflammation, Coagulation and Cardiovascular Diseases," *Canadian J. Cardiol.*, vol. 26:e140-e145, 2010.
Saas et al., "Phosphatidylserine-Expressing Cell By-Products in Transfusion: A Pro-Inflammatory or an Anti-Inflammatory Effect?," *Transfus Clin Biol.*, vol. 19(3):90-97, 2012.
Stewart et al., "Revision of the 1996 Working Formulation for the Standardization of Nomenclature in the Diagnosis of Lung Rejection," *J. Heart Lung Transplant.*, vol. 26:1229-1242, 2007.
Takahashi et al., "The Role of Microparticles in Chronic Obstructive Pulmonary Disease," *Inter. J. COPD*, vol. 9:303-314, 2014.
The ARDS Definition Task Force, "Acute Respiratory Distress Syndrome," *JAMA*, vol. 307(23):2526-2533, 2012.
Todd et al. "Bronchiolitis Obliterans Syndrome: The Final Frontier for Lung Transplantation," *Chest*, vol. 140:502-508, 2011.
Tyurin et al., "Oxidatively Modified Phosphatidylserines on the Surface of Apoptotic Cells are Essential Phagocytic 'eat-me' Signals: Cleavage and Inhibition of Phagocytosis by Lp-PLA$_2$," *Cell Death Differ.*, vol. 21:825-835, 2014.
Wenche et al., "Microparticles in Stored Red Blood Cells as Potential Mediators of Transfusion Complications," *Transfusion*, vol. 51:886-893, 2011.
Zhao et al., "Thrombospondin-1 Triggers Macrophage IL-10 Production and Promotes Resolution of Experimental Lung Injury," *Mucosal Immunol.*, vol. 7:440-448, 2014.
Hazen, "Oxidized Phospholipids as Endogenous Pattern Recognition Ligands in Innate Immunity," *J Biol Chem* 283(23):15527-15531, 2008.

\* cited by examiner

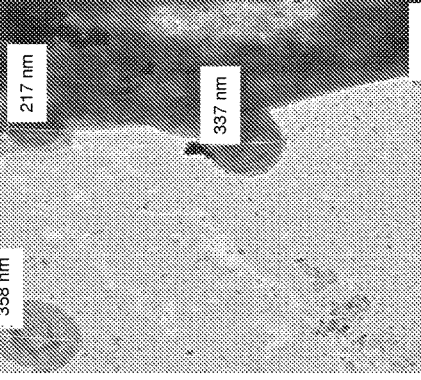
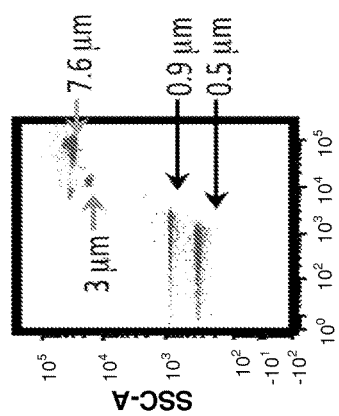
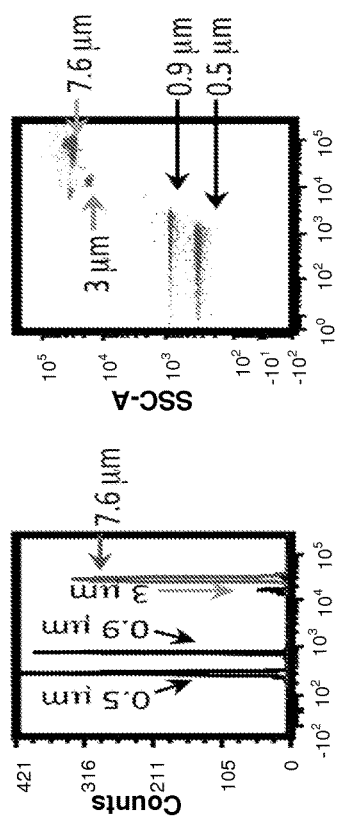
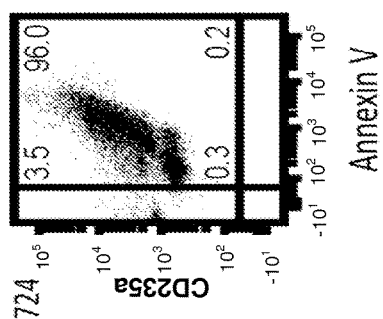
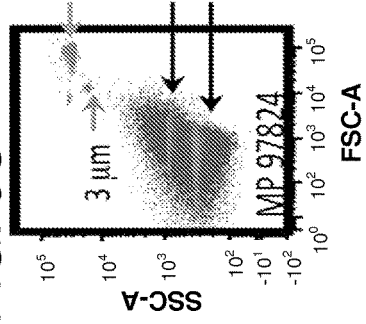

RED BLOOD CELL MEMBRANE-DERIVED MICROPARTICLES AND THEIR USE FOR THE TREATMENT OF LUNG DISEASE

CROSS REFERENCE TO RELATED APPLICATIONS

This is the U.S. National Stage of International Application No. PCT/2014/064352, filed Nov. 6, 2014, published in English under PCT Article 21(2), which claims the benefit of U.S. Provisional Application No. 61/901,247, filed Nov. 7, 2013, which is incorporated herein by reference in its entirety.

ACKNOWLEDGMENT OF GOVERNMENT SUPPORT

This invention was made with government support under grant numbers HL086884, RR024153 and TR000005 awarded by the National Institutes of Health. The government has certain rights in the invention.

FIELD

This disclosure concerns red blood cell (RBC) membrane-derived microparticles (MPs) as immunomodulatory agents, such as for the treatment of lung disease.

BACKGROUND

Lung transplantation is often the only treatment option for individuals with end-stage lung diseases. However, chronic allograft rejection, which manifests as bronchiolitis obliterans (OB), is the major cause of death beyond the first year following transplantation, and a major contributor to the currently low 5 year survival rate (55%). OB is characterized by airflow limitation that is not reversible and is often progressive. It is also associated with lesions in the smallest airways (~1 mm). Despite advancements in immunosuppression and management of these patients, OB remains a major obstacle in the survival of lung transplant recipients. Thus, there is an unmet need to define immunomodulatory strategies in the lung transplant population which can be provided at a low systemic toxicity risk, yet be delivered to specific target regions at high therapeutic concentrations.

Cell-based therapy shows considerable potential as an immunomodulatory strategy for a variety of lung diseases. Novel techniques to target delivery of these therapies by inhaled aerosol would avoid first-pass metabolism, prevent systemic toxicity, and allow for localized treatment in the small airways at the site of OB.

SUMMARY

Disclosed herein are red blood cell membrane-derived microparticles (RBC MPs) as a cell-based therapy for the treatment of lung disease. RBC MPs are small, lipid membrane vesicles characterized by the presence of phosphatidylserine (PS) on their surface. In some cases, such as when used for therapeutic purposes, the RBC MPs are depleted of hemoglobin. RBC MPs can be administered by inhalation, thereby minimizing toxicity and allowing for localized delivery to relevant sites of disease in the lung.

Provided herein is a method of treating a subject having a lung disease by selecting a subject with a lung disease and administering to the subject by inhalation a therapeutically effective amount of RBC MPs, wherein the RBC MPs are depleted of hemoglobin. The lung disease can be any lung disease that would benefit therapeutically from suppression of immune responses in the lung. In some embodiments, the lung disease is chronic obstructive pulmonary disease (COPD), reactive airway disease such as asthma, bronchiolitis, acute lung injury, lung allograft rejection (acute or chronic), pulmonary fibrosis, interstitial lung disease or hypersensitivity pneumonitis.

Also provided are engineered or artificial RBC MPs comprising (or enriched with) biosynthesized oxidizable PS. In some embodiments, the oxidizable PS comprises stearoyl-linoleoyl-PS (SLPS) or dilinoleoyl-PS (DLPS). Further provided are compositions comprising the engineered or artificial RBC MPs disclosed herein.

The foregoing and other objects, features, and advantages of the invention will become more apparent from the following detailed description, which proceeds with reference to the accompanying figures.

BRIEF DESCRIPTION OF THE DRAWINGS

(FIG. 2A) RBCs were oxidized with $H_2O_2$ (1 mM, 30 minutes). Twenty-six % of $H_2O_2$ treated damaged RBCs (oxRBCs) from C57Bl/6 mice bear surface PS, as evidenced by AnnexinV$^+$7-AAD$^{neg}$ staining by flow cytometric analysis. (FIG. 2B) OxRBCs were injected into wild-type mice by tail vein ($10^9/400$ μL). IL-10 concentrations were measured in liver homogenates after mice were sacrificed at 0 and 96 hours. IL-10 is expressed as pg/mL in 100 μg protein from liver homogenate. *p<0.01, each data point indicates an individual mouse. Data represented as mean+/−SEM.

(FIG. 5A) SN of packed RBC (PRBC) units augment LPS-induced IL-10 production by PBMCs and inhibition of this effect by GST or Thio-CD36 peptide containing the CD36 LIMP-II Emp sequence homology (CLESH) domain. p<0.005, comparing LPS+10% PRBC SN to CLESH containing conditions or LPS only, each point indicates data from individual well conditions from one experiment. Experiments were performed 3 times using 3 different buffy coat donors and 3 different PRBC SN. (FIG. 5B) PBMCs and (FIG. 5C) CD14-magnetic bead isolated mononuclear phagocytes from explanted human lung tissues deemed unsuitable for transplantation (due to pulmonary embolus, or atelectasis) incubated with increasing concentrations of isolated RBC-derived MPs from PRBC (PRBC MP) in the presence or absence of Thio-CLESH. ½×, 1×, 2×PRBC MP correspond to 10, 20 and 40 μL of MP concentrate (which corresponds to ~5, 10, 20 mL blood from non-LR PRBC units). Representative of experiments performed 3 independent times for (B). Combined data using 1 human lung tissue explant utilizing RBC-derived MPs from 2 different PRBC units, with each point indicating data from individual well conditions for (B), p<0.01, *p<0.05.

FIGS. 6A-6E: Identification, sizing and relative enumeration of human ghost RBC MPs by flow cytometric analysis. (FIG. 6A) Histogram in the FL-1 (FITC) channel showing fluorescent microbeads of different sizes that were utilized for ghost MP enumeration (0.5, 0.9, 3, 7.6 microns). (FIG. 6B) Side scatter channel (SSC) representing granularity and forward scatter channel (FSC) representing size (note log axis) identifies the beads of various sizes and their appearances. (FIG. 6C) Overlay of microbeads and RBC ghost MPs indicate that ghost MPs are sub-micron in size. The number of events generated by ghost MPs (97824) relative to the number of events generated by the 7.6 micron beads (724) allows for relative enumeration since the absolute numbers of 7.6 micron beads in the sample well is known. (FIG. 6D) Ghost MPs show surface glycophorin A (CD235a) and Annexin V binding (which avidly binds PS). (FIG. 6E) EM image of ghost RBC with blebbing of MPs showing similar sizing of particles.

(FIG. 7A) BAL total leukocyte counts, (FIG. 7B) total PMN counts, and (FIG. 7C) total protein concentrations were obtained. *p<0.05, two-tailed Mann-Whitney test, n=8 mice/gp.

(FIG. 9A) Transmission electron microscopy image of ghost RBC-derived MPs (scalebar=600 nm). (FIG. 9B) LPS-induced IL-10 production by human PBMCs is enhanced with ghost MPs (ghMP) in a concentration-dependent fashion. All samples were assayed in duplicate. Data represents combined values from two independent studies using PBMCs from two healthy volunteers. (FIG. 9C) LPS-induced IL-10 production by human PBMCs is enhanced with ghMPs. PBMCs were pre-incubated in the absence or presence of CLESH peptide (0, 1, 10 μg) for 1 h, then stimulated with LPS (10 ng/mL) for another hour. ghMPs were added to select wells at 4 μg and PBMCs were incubated for 18 hours. Supernatants were collected and assayed for IL-10. The data was obtained from separate well conditions using PBMCs from healthy volunteers and is representative of two independent experiments (p<0.001, *p<0.0001).

DETAILED DESCRIPTION

Figure 1:
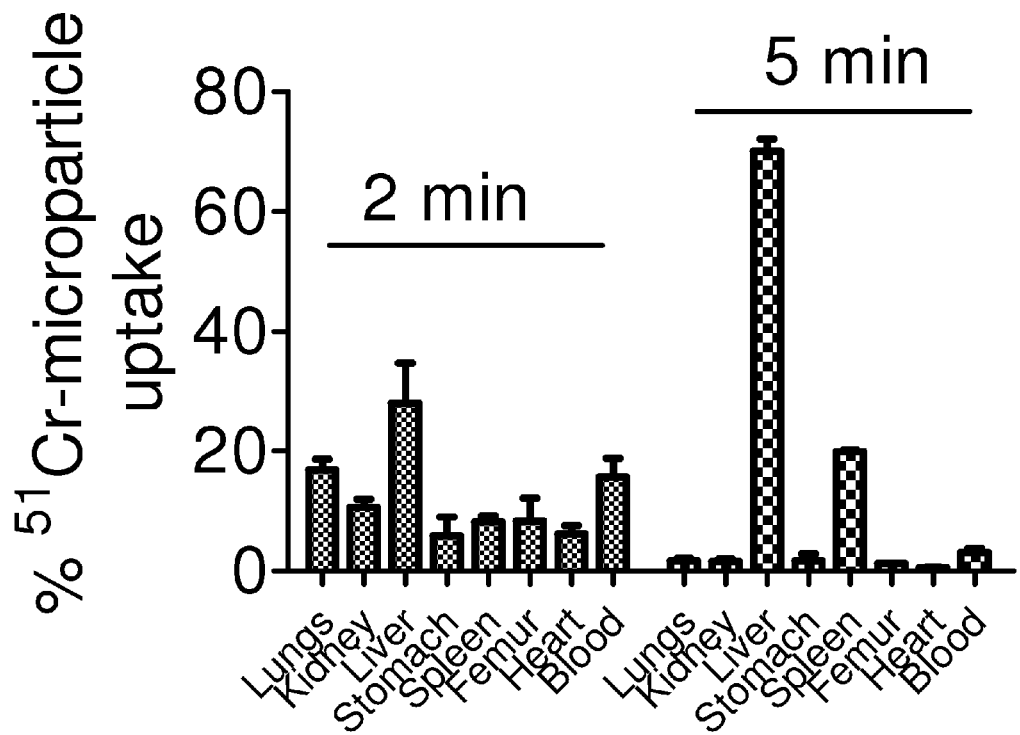
FIG. 1: RBC MPs from standard RBC unit are taken up by the mononuclear phagocyte system of the liver and spleen in vivo. RBC MPs were isolated from an expired standard RBC unit from the blood bank using previously described method (Xiong et al., *Transfusion*. 2011; 51(3): 610-621), and labeled with $^{51}Cr$ as previously described (Willekens et al., *Blood*. 2005; 105(5):2141-2145). Mice were injected with $^{51}Cr$-labeled MPs by tail vein, euthanized at the indicated time points, and each organ was harvested, weighed, and gamma counts measured in a counter. Percent $^{51}Cr$ uptake reflects percentage of gamma counts to total counts administered. n=3 mice at each time point.

I. Abbreviations
  BAL bronchoalveolar lavage
  BSA bovine serum albumin
  CLESH CD36 LIMP-II Emp sequence homology
  COPD chronic obstructive pulmonary disorder
  DLPS dilinoleoyl-PS
  EM electron microscopy
  FITC fluorescein isothiocyanate
  ghMPs ghost microparticles
  Hb hemoglobin
  HMDM human monocyte-derived macrophages
  HPLC high-performance liquid chromatography
  IL interleukin
  i.t. intratracheal
  LDL low density lipoprotein
  LPS lipopolysaccharide
  Mφ macrophage
  MFI mean fluorescence intensity
  MOC micro-orifice collector
  MP microparticle
  NO nitric oxide
  OB bronchiolitis obliterans
  PBMC peripheral blood mononuclear cell
  PBS phosphate buffered saline
  PE phycoerythrin
  PMN polymorphonuclear PRBC packed red blood cell
PS phosphatidylserine
RBC red blood cells
SCC side scatter channel
SLPS stearoyl-linoleoyl-PS
SN supernatant
TNF tumor necrosis factor II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Acute: A disease or disorder of short duration, generally characterized by severe symptoms and rapid progression. This term is used in contrast to "chronic".

Acute lung allograft rejection: A condition occurring after lung transplantation that is characterized by the presence of perivascular and interstitial mononuclear cell infiltrates. The intensity of the perivascular mononuclear cell cuffs and the distribution of the mononuclear cells, including extension beyond the vascular adventitia into adjacent alveolar septa, form the basis of the histologic grade (A1-A4; Stewart et al., *J Heart Lung Transplant* 26:1229-1242, 2007).

Acute lung injury (ALI): A pulmonary disorder that can be induced directly by inhalation of toxic chemicals (chemical induced acute lung injury) or other means or can be induced indirectly by systemic injury. Acute lung injury includes subcategories of respiratory distress syndromes including infant respiratory distress syndrome (IRDS), hyaline membrane disease (HMD), neonatal respiratory distress syndrome (NRDS), respiratory distress syndrome of newborn (RDSN), surfactant deficiency disorder (SDD), acute respiratory distress syndrome (ARDS), respiratory complication from systemic inflammatory response syndrome (SIRS), or severe acute respiratory syndrome (SARS). ALI is characterized by dyspnea, hypoxemia, and diffuse infiltrates on chest x-ray with respiratory failure not fully explained by cardiac failure or fluid overload (ARDS Definition Task Force, *JAMA* 307(23):2526-2533, 2012). The degree of hypoxemia in ALI can be categorized as mild, moderate, and severe based upon the ratio of arterial oxygen partial pressure over inspiratory oxygen fraction ($PaO_2/FiO_2$)≤300 but >200 (which is sometimes referred to as mild ARDS), $PaO_2/FiO_2$<200 but >100 (referred to as moderate ARDS), or $PaO_2/FiO_2$<100 (which is referred to as severe ARDS; based upon most current Berlin Definition of ARDS, ARDS Definition Task Force, *JAMA* 307(23):2526-2533, 2012). Diagnosis is usually made by clinical presentation, ABGs (arterial blood gas analyses) and imaging studies. Standard treatment methods include lung-protective, low tidal volume mechanical ventilation and supportive therapy. Acute hypoxemic respiratory failure is due to non-cardiogenic pulmonary edema (reviewed in Honing, E. G., and Ingram, R. H., Jr., in: *Harrison's Principles of Internal Medicine*, 14th Edition, A. S. Fauci, et al. (eds.), McGraw-Hill, N.Y., pp. 1483-1486, 1998; and Goodman, R. B., et al., *Am J. Respir. Crit. Care Med.* 154:602-11, 1996). ALI develops rapidly after a predisposing condition triggers a systemic inflammatory response, and is most strongly associated with conditions that produce direct alveolar injury or direct injury via the pulmonary capillary bed, such as aspiration, diffuse infection, toxic inhalation, direct injury to the alveolar epithelium, or sepsis syndrome. ALI can be the consequence of unregulated over-expression of usual systemic inflammatory responses to infection and/or injury. ALI can also occur in the absence of leukocyte mediated events and therefore is not always associated with inflammation. Injury involves the alveolar epithelium and the pulmonary capillary endothelium, and results in a complex cascade of events. Injury is produced by cellular events associated that can include loss of epithelial and endothelial barrier function aggravated by activation of neutrophils, macrophages, monocytes, and lymphocytes producing various cytokines, in turn producing cellular activation, chemotaxis, and adhesion.

Administration: Administration of an active compound or composition (such as a RBC membrane-derived microparticle), which can occur by any route known to one of skill in the art. Administration can be local or systemic. Examples of local administration (also referred to as "local delivery") include, but are not limited to, topical administration, subcutaneous administration, intramuscular administration, intrathecal administration, intrapericardial administration, intra-ocular administration, topical ophthalmic administration, or administration to the nasal mucosa or lungs by inhalational administration (for example, by aerosol delivery). Systemic administration includes any route of administration designed to distribute an active compound or composition widely throughout the body via the circulatory system. Thus, systemic administration includes, but is not limited to intra-arterial and intravenous administration. Systemic administration also includes, but is not limited to, topical administration, subcutaneous administration, intramuscular administration, or administration by inhalation, when such administration is directed at absorption and distribution throughout the body by the circulatory system.

Aerosol: A gaseous suspension of fine solid or liquid particles, such as a suspension of a drug or other substance to be dispensed in a cloud or mist. Aerosol delivery refers to administration (such as to the airway) of a therapeutic agent that is formulated as an aerosol.

Asthma: A chronic condition involving the respiratory system in which the airways constrict, become inflamed and are lined with excessive amounts of mucus, often in response to one or more triggers. Episodes of asthma can be triggered by a number of different factors, such as exposure to an environmental stimulant, such as an allergen, environmental tobacco smoke, cold or warm air, perfume, pet dander, moist air, exercise or exertion, or emotional stress. In children, the most common triggers are viral illnesses such as those that cause the common cold. The airway narrowing that occurs in asthma causes symptoms such as wheezing, shortness of breath, chest tightness and coughing.

Bronchiolitis: Inflammation of the bronchioles, the smallest air passages of the lungs. The term often refers to acute viral bronchiolitis, a common disease in infancy, usually caused by respiratory syncytial virus or other viruses including metapneumovirus, influenza, parainfluenza, coronavirus, adenovirus and rhinovirus. Obliterative bronchiolitis (also known as bronchiolitis obliterans or constrictive bronchiolitis) is a life-threatening form of non-reversible obstructive lung disease in which the bronchioles are plugged with granulation tissue. Inflammation and scarring occur in the airways of the lung, resulting in severe shortness of breath and dry cough. Obliterative bronchiolitis has many possible causes, including collagen vascular disease, transplant rejection in organ transplant patients, viral infection (e.g., respiratory syncytial virus, adenovirus, human immunodeficiency virus or cytomegalovirus), pneumocystis pneumonia, drug reaction, complications of prematurity (bronchopulmonary dysplasia), and exposure to toxic fumes (such as diacetyl, sulfur dioxide, nitrogen dioxide, ammonia, chlorine, thionyl chloride, methyl isocyanate, hydrogen fluoride, hydrogen bromide, hydrogen chloride, hydrogen sulfide, phosgene, polyamide-amine dyes or ozone). Diffuse panbronchiolitis (DPB) is an inflammatory lung disease (considered to be a type of COPD) with no known cause. DPB is a severe, progressive form of bronchiolitis, mainly affecting the respiratory bronchioles (the section of the bronchioles involved in gas exchange). If left untreated, DPB is fatal, usually progressing to bronchiectasis, an irreversible lung condition that causes respiratory failure. Post-transplant bronchiolitis refers to inflammation of bronchioles following lung transplant.

Chronic: A "chronic" disease or disorder is a condition that persists for a long period of time. Any disease or disorder that persists for at least three months is generally considered a "chronic" disease or disorder.

Chronic lung allograft rejection: A condition occurring after lung transplantation that is associated with obliterative bronchiolitis, which describes dense eosinophilic hyaline fibrosis in the sub-mucosa of membranous and respiratory bronchioles, resulting in partial or complete luminal occlusion (Stewart et al., *J Heart Lung Transplant* 26:1229-1242, 2007). It is also associated with bronchiolitis obliterans syndrome (BOS) which is clinically defined as progressive airflow obstruction unexplained by acute rejection, infection, or other confounding complication (Todd and Palmer, *Chest* 140(2):502-508, 2011).

Chronic obstructive pulmonary disease (COPD): A disease of the lungs in which the airways become narrowed, leading to a limitation of the flow of air to and from the lungs, which causes shortness of breath. In contrast to asthma, the limitation of airflow is poorly reversible and usually gradually gets worse over time. COPD is caused by noxious particles or gases, most commonly from smoking, which trigger an abnormal inflammatory response in the lung. The inflammatory response in the larger airways is known as chronic bronchitis, which is diagnosed clinically when people regularly cough up sputum. In the alveoli, the inflammatory response causes destruction of the tissue of the lung, a process known as emphysema. The natural course of COPD is characterized by occasional sudden worsening of symptoms called acute exacerbations, most of which are caused by infections or air pollution. COPD is also known as chronic obstructive lung disease, chronic obstructive airway disease, chronic airflow limitation and chronic obstructive respiratory disease. As an example, emphysema is one type of COPD.

Depleted of hemoglobin: Refers to a RBC MP in which hemoglobin (Hb) has been substantially removed, such as by removing the cytosolic contents of the RBC (e.g., by lysis). In the context of the present disclosure, "depleted of hemoglobin" does not require a complete absence of Hb, but generally refers to an RBC MP in which the Hb has been substantially depleted, such as about 90%, about 95% or about 99% depleted.

Ghost RBC: A red blood cell membrane depleted of cytosolic contents. A ghost RBC is substantially depleted of Hb.

Hypersensitivity pneumonitis: An inflammation of the alveoli within the lung caused by hypersensitivity to inhaled organic dusts.

Inhaler: An apparatus for administering vapor or volatilized medications by inhalation. Inhalers are often used to administer medication locally to the airway, for example to treat asthma. In some examples, the inhaler is a dry powder inhaler. In other examples, the inhaler is a metered-dose inhaler.

Interstitial lung disease: A group of lung diseases affecting the interstitium (the tissue and space around the air sacs of the lungs). Interstitial lung disease is also known as diffuse parenchymal lung disease.

Lung disease: Includes any disease or disorder that affects the lungs. In particular examples, the lung disease is a chronic lung disease that lasts for more than three months. In other embodiments, the lung disease is a chronic progressive disease that worsens over time absent treatment that interferes with the progression of the disease. Exemplary lung diseases include, but are not limited to, chronic obstructive pulmonary disease (COPD), asthma, bronchiolitis, post-transplant bronchiolitis, acute lung injury, lung allograft rejection (acute or chronic), pulmonary fibrosis, interstitial lung disease and hypersensitivity pneumonitis.

Nebulizer: A device that turns liquid forms of medicine into a fine spray (aerosol) that can be inhaled, especially for delivering medication to the deep part of the respiratory tract.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In some embodiments, the pharmaceutically acceptable carrier is suitable for delivery to an airway. Carriers for airway delivery are well known in the art and are discussed below.

Phosphatidylserine (PS): A phospholipid component, usually found on the inner-leaflet (cytosolic side) of cell membrane. However, when a cell undergoes apoptosis, PS becomes exposed on the surface of the cell. The presence of PS on the outer surface of a cell serves as an "eat me" signal for macrophages.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Pulmonary fibrosis: The formation or development of excess fibrous connective tissue in the lungs. Pulmonary fibrosis can be a secondary effect of another disease, such as an interstitial lung disease, but can also occur without any known cause (referred to as idiopathic pulmonary fibrosis).

Red blood cell (RBC): The most common type of blood cell, responsible for delivering oxygen to body tissues. The cytoplasm of a RBC is rich in hemoglobin, an iron-containing molecule that can bind (and later release) oxygen. RBCs are also known as erythrocytes.

Red blood cell membrane-derived microparticle (RBC MP): A small (generally less than 1000 nm) vesicle derived from the lipid membrane of a RBC. In addition to their size, RBC MPs are characterized by the presence of glycophorin A (a transmembrane antigen specific to erythrocytes) and expression of phosphatidylserine (PS) on their surface. In some embodiments of the present disclosure, RBC MPs are derived from "ghost RBCs" and are therefore depleted of hemoglobin. Generally, ghost RBC MPs are produced by lysing RBCs with hypotonic buffer and washing to remove cytosolic components, including hemoglobin. The RBC-derived membranes re-seal spontaneously and a series of centrifugation and wash steps are used to isolate RBC MPs of the desired size. Methods of making RBC MPs are described in the Examples below (see in particular Example 5). In some embodiments, the RBC MPs are engineered to express higher levels of PS on their surface and/or to increase the amount of (or ratio of) oxidized or oxidizable PS on their surface; these RBC MPs are referred to herein as "engineered RBC MPs." Engineered RBC MPs can optionally include additional proteins and/or other components. As used herein, an "artificial RBC MP" refers to an artificially-prepared liposome composed of a lipid bilayer and the surface markers characteristic of a RBC MP, including PS (such as oxidized and/or oxidizable PS) expressed on the surface.

Subject: Living multi-cellular vertebrate organisms, a category that includes both human and non-human mammals.

Therapeutically effective amount: A quantity of a specified pharmaceutical agent sufficient to achieve a desired effect in a subject, or in a cell, being treated with the pharmaceutical agent. For example, this can be the amount of an RBC membrane-derived microparticle for the treatment of acute lung injury. The effective amount of the pharmaceutical agent will be dependent on several factors, including, but not limited to the subject or cells being treated, and the manner of administration of the therapeutic composition.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control.

In addition, the materials, methods, and examples are illustrative only and not intended to be limiting.

III. Overview of Several Embodiments

Cell-based therapies show considerable potential as an immunomodulatory strategy for a variety of lung diseases, including COPD, asthma, bronchiolitis, acute lung injury, acute lung allograft rejection, chronic lung allograft rejection, pulmonary fibrosis, interstitial lung disease and hypersensitivity pneumonitis. Described herein is the development and characterization of red blood cell membrane-derived microparticles (RBC MPs) for the treatment of lung disease. RBC MPs are small (less than 1000 nm), lipid membrane vesicles characterized by the presence of PS on their surface. In some embodiments, the RBC MPs are depleted of Hb to enable their use for the therapeutic purposes described herein. It is disclosed herein that administration of RBC MPs to the lung via inhalation promotes the production of immunoregulatory cytokines (such as IL-10), and reduces inflammation and injury in the lung.

Provided herein is a method of treating a subject having a lung disease, comprising selecting a subject with a lung disease and administering to the subject by inhalation a therapeutically effective amount of RBC MPs, wherein the RBC MPs are depleted of hemoglobin, or a therapeutically effective amount of artificial RBC MPs. The lung disease can be any lung disease that would benefit therapeutically from suppression of immune responses in the lung. In some embodiments, the lung disease is chronic obstructive pulmonary disease (COPD), asthma, bronchiolitis, acute lung injury, acute lung allograft rejection, chronic lung allograft rejection, pulmonary fibrosis, interstitial lung disease or hypersensitivity pneumonitis.

Inhalation administration of RBC MPs (including artificial RBC MPs) can be achieved using any suitable formulation and delivery device to enable delivery of the RBC MPs to the appropriate sites in the lung, such as the small airways. In some embodiments, the RBC MPs are administered as a liquid aerosol for inhalation. In other embodiments, the RBC MPs are administered as a dry powder for inhalation. In some embodiments, the RBC MPs are administered using a nebulizer, metered dose inhaler or dry powder inhaler.

In some embodiments, the RBC MPs are about 100 to about 1000 nm in diameter, such as about 100, about 200, about 300, about 400, about 500, about 600, about 700, about 800, about 900 or about 1000 nm in diameter. In some examples, the RBC MPs are about 100 to about 400 nm in diameter. In particular examples, the RBC MPs are about 200 to about 300 nm in diameter.

The RBC MPs can be generated, for example, from stored blood using any technique known in the art. Exemplary protocols are provided herein as Example 5.

In some embodiments, the RBC MPs are engineered to contain additional or modified surface markers. For example, the RBC MPs can be engineered to be enriched in oxidizable and/or oxidized PS. In particular examples, the oxidizable PS comprises biosynthesized oxidizable stearoyl-linoleoyl-PS (SLPS) or dilinoleoyl-PS (DLPS).

Further provided herein are engineered RBC MPs that are engineered to express higher levels of PS on their surface and/or engineered to increase the amount of (or ratio of) oxidized or oxidizable PS on their surface (relative to naturally derived and unaltered RBC MPs). In some embodiments, the engineered RBC MPs are depleted of hemoglobin. In some embodiments, the engineered RBC MPs comprise biosynthesized oxidizable SLPS or DLPS.

Engineered RBC MPs can optionally include additional proteins and/or other components in their membranes.

Also provided herein are artificial RBC MPs. In some embodiments, the artificial RBC MPs are comprised of artificial liposomes. Artificial RBC MPs contain surface markers characteristic of a RBC MP, including PS (such as oxidized and/or oxidizable PS) expressed on the surface. Artificial RBC MPs also do not contain Hb. In some embodiments, the artificial RBC MPs comprise biosynthesized oxidizable SLPS or DLPS. As with engineered RBC MPs, artificial RBC MPs can optionally include additional surface markers or other components within the liposomal membrane.

In some embodiments, the engineered or artificial RBC MPs are about 100 to about 1000 nm in diameter, such as about 100, about 200, about 300, about 400, about 500, about 600, about 700, about 800, about 900 or about 1000 nm in diameter. In some examples, the engineered or artificial RBC MPs are about 100 to about 400 nm in diameter. In particular examples, the RBC MPs are about 200 to about 300 nm in diameter.

Further provided herein are compositions comprising an engineered or artificial RBC MP disclosed herein and a pharmaceutically acceptable carrier. In some embodiments, the RBC MP-containing compositions are formulated for administration by inhalation. In some examples, the engineered or artificial RBC MPs are formulated as a liquid aerosol. In other examples, the engineered or artificial RBC MPs are formulated as a dry powder.

IV. Use of RBC MPs for the Treatment of Lung Disease

More than 30 years ago, the phenomenon of transfusion-related immunomodulation (TRIM) was recognized with the observation that individuals receiving RBC transfusion prior to renal transplantation had increased allograft survival compared to those not transfused (Opelz et al., *Lancet.* 1981; 1(8232): 1223-1225; Opelz et al., *Transplant Proc.* 1973; 5(1):253-259; Opelz and Terasaki, *N Engl J Med.* 1978; 299(15):799-803). In fact, prior to the advent of immunosuppression with cyclosporine, RBC transfusion was used to deliberately prevent allograft rejection (Vamvakas and Blajchman, *Blood Rev.* 2007; 21(6):327-348). What is remarkable about this observation (validated by multiple centers) is that increased allograft survival was not accompanied by increased infectious complications. Although the mechanism remains elusive, the notion of TRIM has evolved to encompass the growing recognition in the field that allogeneic leukocytes are not the sole potential source of this effect and that both pro-inflammatory in addition to immunoregulatory responses may be induced (Vamvakas and Blajchman, *Blood Rev.* 2007; 21(6):327-348). Harnessing the immunoregulatory factor in RBC transfusates, and directly providing this factor to the small airways and airspaces, provides a way to address a number of lung diseases, including chronic allograft rejection in the lungs that presents itself as bronchiolitis obliterans (OB).

A. RBC Membrane-derived MPs as a Platform for Reprogramming Airspace Macrophages During Aberrant Inflammation Stored RBCs undergo a number of morphologic and biochemical changes collectively termed the "storage lesion" (Tinmouth and Chin-Yee, *Transfus Med Rev.* 2001; 15(2):91-107; Tinmouth et al., *Transfusion.* 2006; 46(11): 2014-2027), as storage conditions favor the shift in the local redox potential towards oxidant stress (Wagner et al., *Blood.* 1987; 69(6):1777-1781; Wolfe et al., *J Clin Invest.* 1986; 78(6):1681-1686). This shift results in lipid peroxidation (Tinmouth and Chin-Yee, *Transfus Med Rev.* 2001; 15(2): 91-107), membrane and cytoskeletal protein oxidation (Dumaswala et al., *Blood.* 1996; 88(2):697-704), resulting in hemolysis and MP formation (Dumaswala et al., *Blood.* 1996; 88(2):697-704; Greenwalt et al., *Vox Sang.* 1984; 47(4):261-270). RBC-derived MPs show loss of phospholipid asymmetry and express PS on their surface, and are rapidly cleared by the liver Kupffer cells mainly through scavenger receptors, as the uptake by the liver could be inhibited by preinjection of the scavenger-receptor ligands polyinosinic acid and phosphatidylserine (Willekens et al., *Blood.* 2005; 105(5):2141-2145). Although externalized PS is a well-known "eat-me" signal expressed by apoptotic cells necessary for engulfment in macrophages, and the induction of immuno-suppressive or anti-inflammatory responses during either contact recognition or following engulfment, whether externalized PS on the surface of RBC MPs can alter subsequent immune response during inflammation and injury has not been previously adequately addressed (Ravichandran and Lorenz, *Nat Rev Immunol.* 2007; 7(12):964-974). While virtually all cells release MPs, re-engineering the RBC membrane-derived MP is particularly attractive as there is a long history of safety and blood banking expertise with allogeneic and autologous RBC transfusion and others have utilized RBC membranes as biomimetic nanoparticle delivery platforms in circulation (Merkel et al., *Proc Natl Acad Sci USA.* 2011; 108(2):586-591; Hu et al., *Proc Natl Acad Sci USA.* 2011; 108(27):10980-10985).

The present disclosure contemplates the use of autologous RBCs from subjects that can be re-engineered for aerosol delivery to the lungs. Furthermore, unlike other cell-derived MPs, $PS^+$ RBCs are not considered significant contributors to hemostasis and thrombosis (Zwaal and Schroit, *Blood.* 1997; 89(4):1121-1132). In primates, complement receptor (CR)-1 is expressed by erythrocytes and a major mechanism by which C3b-opsonized immune complexes are cleared by the mononuclear phagocyte system. In addition, CR1 can negatively regulate complement activation by inhibiting C3 convertase and C5 convertase (Iida and Nussenzweig, *J Exp Med.* 1981; 153(5):1138-1150). This mechanism of mitigating complement mediated cellular injury may be important within the airspaces during inflammatory processes, as RBC MPs are enriched for CR1 (Pascual et al., *J Immunol.* 1993; 151(3):1702-1711). Interestingly, C1q and mannose binding lectin (MBL), two structurally similar molecules that are ligands for CR1 and involved in innate immune responses to pathogen, also bind apoptotic cells and function as "eat-me" signals (Ogden et al., *J Exp Med.* 2001; 194(6):781-795). Calreticulin, a multifunctional protein, expressed on the cell surface of phagocytes can also bind C1q and MBL at their collagen domain and mediate the uptake of apoptotic cells through LDL-receptor protein 1 (CD91).

B. Inhalation of RBC Membrane-derived MPs to Suppress Lung Allograft Rejection and Other Lung Diseases Previous studies have utilized a lentiviral vector approach to determine the effect of human IL-10 expression on airway obliteration in a murine tracheal allograft model—a frequently used model of OB/chronic lung transplant rejection. Nearly complete tracheal obstruction was apparent in treatment and control groups at day 28 of the study, as gene expression began to peak. By day 42, obstruction had significantly decreased in the IL-10 group in comparison to the no treatment, and vehicle control groups which still demonstrated nearly complete obliteration (Hirayama et al., *Hum Gene Ther.* 2011; 22(11):1453-1460). Other studies have utilized mesenchymal stem cell therapies to increase IL-10 levels and to decrease IL-6 and TNF-α in a similar tracheal allograft model, resulting in decreased obstruction.

The effect was eliminated if Mφ were removed, implying a similar mechanism to what is proposed herein (Guo et al., *Int Immunopharmacol.* 2013; 15(4):726-734).

Without limiting the invention, it is believed that increasing IL-10 levels in the small airways—the site of the OB lesion—will effectively suppress chronic lung allograft rejection. The immunomodulatory properties of RBC-membrane based MPs include but are not limited to this effect and can be further optimized through re-engineering of the microparticle surface. Inhalation of the MPs allows for direct access to the airways and airspaces, bypasses gastrointestinal/hepatic degradation, minimizes systemic dosing and associated toxicity, and provides the most efficient use of the product available. The inhaled delivery of biological and cell based therapies present unique challenges. Aerosols for inhaled delivery must fall into very specific size ranges in order to reach and deposit into the airways or alveoli. For a human lung, target ranges of 1-5 µm are typically described. Based on the smaller upper airways of the mouse, aerosols in ≤1 µm would likely be necessary for deep lung penetration. Targeting specific lung zones (such as the human small airways) requires precise consideration of aerosol size and control of other factors such as respiratory rate and flow. The shear forces associated with the atomization processes used to produce these aerosols, along with the changes in temperature and hydration associated with aerosol conveyance may affect the biological activity of the therapies. The limited quantities of preparations available during early development also necessitate the use of efficient delivery technologies. The development of aerosol delivery systems that allow for intact and targeted delivery of cells or cell products such as RBC-derived MPs to the murine or human lung would facilitate other new applications of cell-based therapies, a rapidly developing class of therapeutics.

The following examples are provided to illustrate certain particular features and/or embodiments. These examples should not be construed to limit the disclosure to the particular features or embodiments described.

EXAMPLES

Example 1

Production, Characterization and Delivery of RBC MPs

This example describes the generation and characterization of red blood cell membrane-derived microparticles (RBC MPs). This example further demonstrates that administration of RBC MPs to the lung via inhalation promotes the production of immunoregulatory cytokines (such as IL-10), and reduces inflammation and injury in the lung.

RBC-derived MPs are Rapidly Ingested by Macrophages In Vitro and Taken Up by the Mononuclear Phagocyte System In Vivo RBC MPs, defined by glycophorin A (a transmembrane antigen specific to erythrocytes) and size (<1 micron), increase in numbers in the supernatant (SN) of standard RBC units with storage duration and the percentage of MPs expressing surface phosphatidylserine (PS) increases with storage duration (Xiong et al., *Transfusion.* 2011; 51(3):610-621). Data show that these RBC MPs are rapidly ingested by macrophages within minutes in vitro.

Consistent with the findings of Willekens et al. with rat MPs (Willekens et al., *Blood.* 2005; 105(5):2141-2145), it is shown herein that human RBC MPs are also rapidly taken up by the liver within minutes (FIG. 1). Willekens et al. showed that rat MP clearance from the blood, as well as liver uptake, was significantly inhibited by preinjection of the scavenger-receptor ligands polyinosinic acid and PS, providing evidence that scavenger receptors expressed on Kupffer cells are mainly responsible for their clearance (Willekens et al., *Blood.* 2005; 105(5):2141-2145). Thus, RBC MPs target the mononuclear phagocyte system.

Figure 2A:
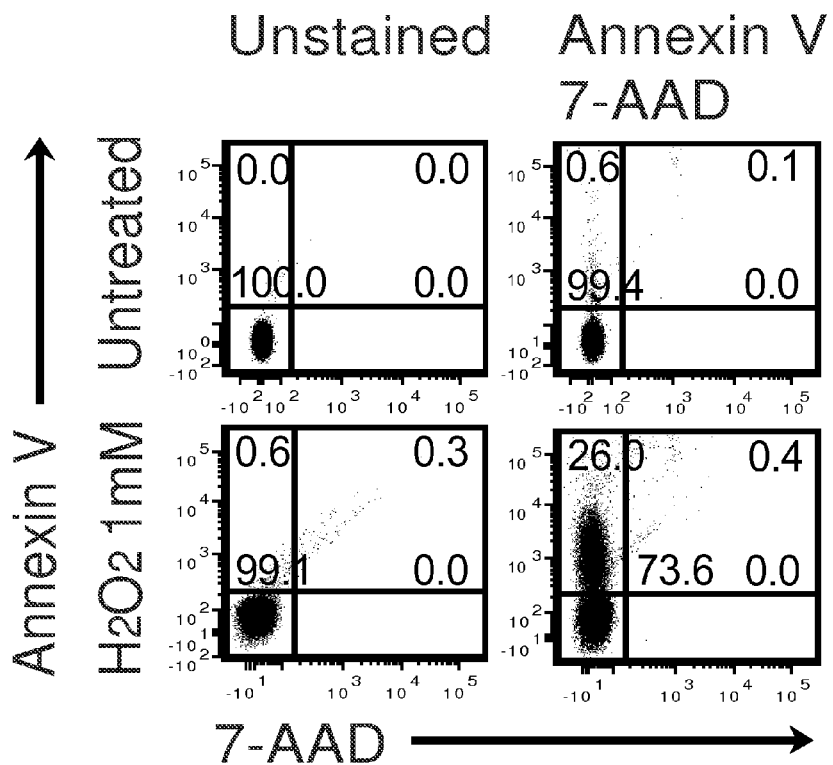
FIGS. 2A-2B: PS+ oxRBC induce liver IL-10 production. Whole blood was obtained from C57Bl/6 mice via cardiac puncture following euthanization, and RBCs was separated by centrifugation and several washes.
Figure 2B:
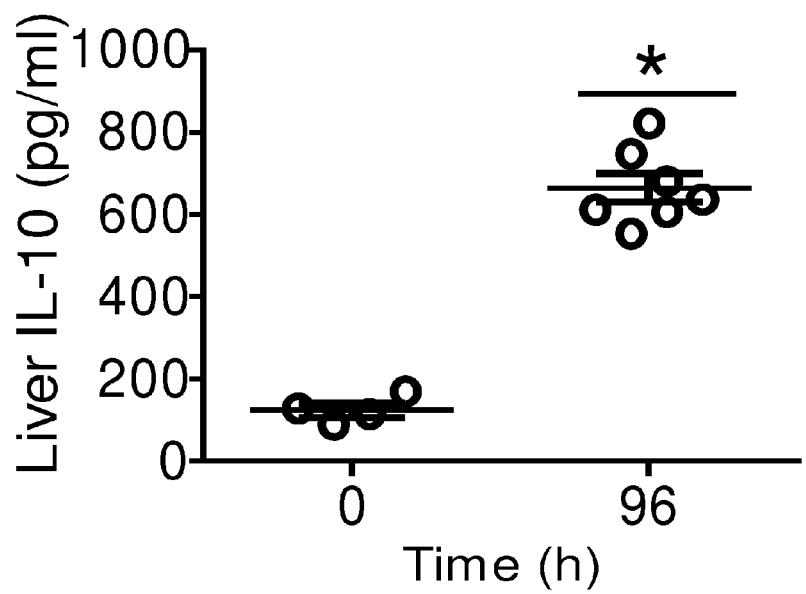

Creation of RBCs with Externalized Phosphatidylserine and Subsequent Transfusion Induces Liver IL-10 Production Apoptotic cells and MPs lose their lipid asymmetry and externalize PS on the surface. To determine whether externalized PS on the surface of cells triggers IL-10 production in vivo, damaged, oxidized RBCs expressing surface PS were created using syngeneic murine RBCs. A model of RBC transfusion was used, as previous reports have shown that aged or damaged RBCs are rapidly cleared from the circulation by the mononuclear phagocyte system in the liver via a polyinosinic-acid and PS-recognizing scavenger receptor (Terpstra and van Berkel, *Blood.* 2000; 95(6):2157-2163). However, others have shown that apoptotic cells attenuate liver hepatitis/injury by priming Kupffer cells (macrophages) to produce IL-10, but peak induction of IL-10 in the liver occurred 3-7 days following apoptotic cell administration. Guided by these studies, mice transfused with $PS^+$ RBCs were obtained. A significant liver induction of IL-10 was observed at 96 hours, the time of harvest (FIG. 2).

Exposure to Supernatant from Standard Blood Bank RBC Units During Mφ Activation Increases Mφ Secretion of the Immune-Regulatory Cytokine IL-10 and Decreases their Secretion of the Pro-inflammatory Cytokine TNF-α

Figure 3B:
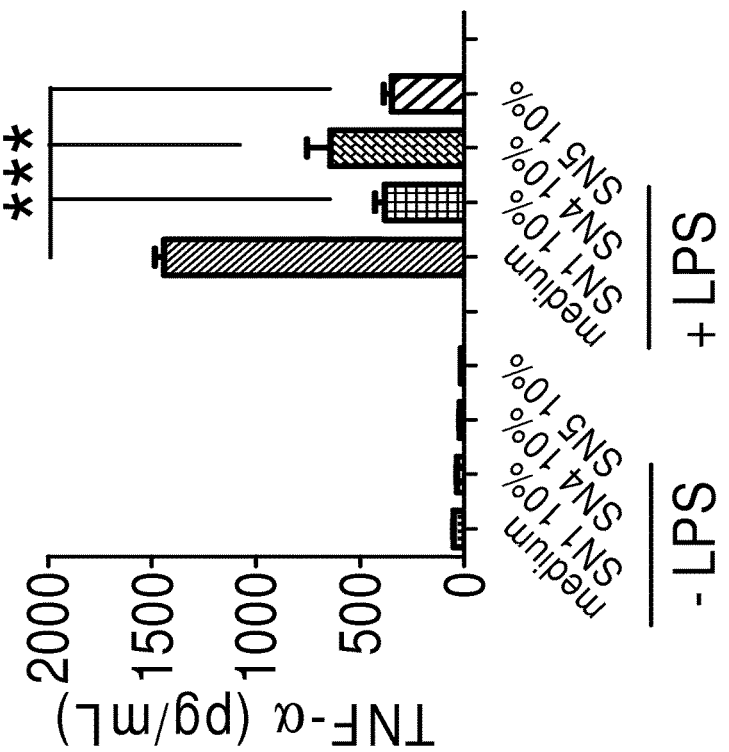
FIGS. 3A-3B: Exposure to SN of RBC units during Mφ activation results in increases in IL-10 production and a suppressive effect on LPS-induced TNF-α production by peritoneal macrophages. Murine peritoneal macrophages were harvested from C57Bl/6 mice 4 days following thioglycollate stimulation. Mφ were stimulated with SN obtained from standard non-leukoreduced RBC units (SN1 at day 31, SN2 at day 37, SN3 at day 37, SN4 at day 37, SN5 at day 38 of storage) in media containing 10% FBS. LPS *E. coli* 011:B4 at 10 ng/mL was used to stimulate IL-10 and TNF-α production in macrophages in the presence or absence of SN. SN from banked RBC units was obtained after centrifugation of blood at 2000 g for 20 minutes at 4° C. The percentage of SN added to each well is indicated on the X-axis. SNs were stored as 1 mL aliquots at −80° C. until use. Shown is the production of IL-10 (FIG. 3A) and TNF-α (FIG. 3B). Performed in triplicates, ***p<0.001, ANOVA, comparing to medium alone.
Figure 3A:
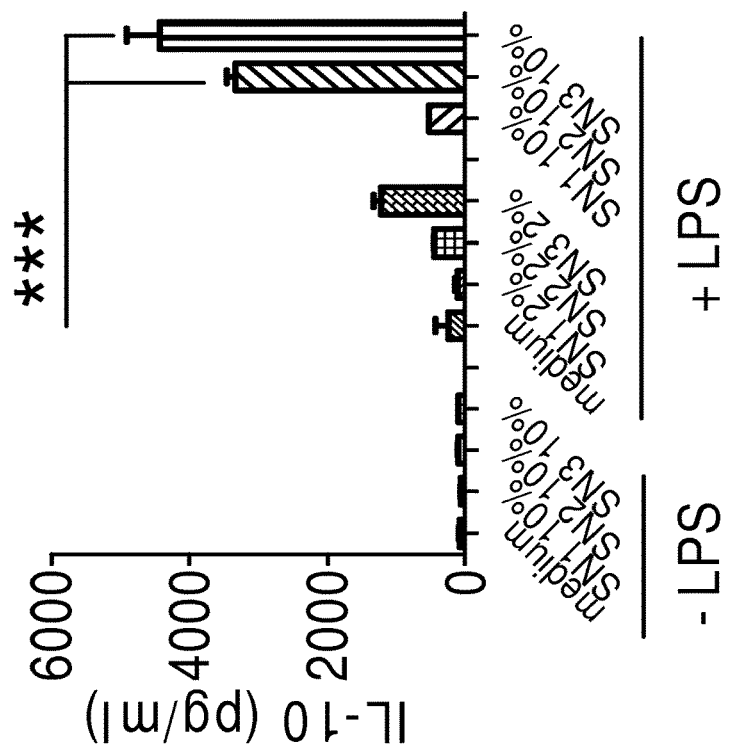

As RBC MPs accumulate in the SN of PRBC units, it was initially tested whether SN of PRBC units could induce IL-10 production in macrophages in vitro. Recognizing the pro-oxidative and potentially inflammatory effect of Hb-derived substances that are also contained in RBC units, Mφ responses to SN of RBC units were assessed in the presence of serum (that normally contains scavenging proteins that bind both free Hb and heme). It was shown that a suppressive effect of RBC SN occurred that is concentration dependent and it was found within the 5 random non-leukoreduced RBC units tested. Without limiting the invention, it is believed that MPs contained in the SN of RBC units provide this immunomodulatory effect and may serve as an additional countering mechanism to the pro-oxidative, cytotoxic, and inflammatory effects of RBC breakdown. Others have previously shown that the presence of apoptotic cells (irradiated lymphocytes) increases the secretion of the anti-inflammatory cytokine IL-10 and decreases secretion of the pro-inflammatory cytokines TNF-α, IL-1β, and IL-12 during LPS-induced human monocyte activation (Voll et al., *Nature.* 1997; 390(6658):350-351). Voll et al. (*Nature.* 1997; 390(6658):350-351) and others (such as Erwig and Henson, *Am J Pathol.* 2007; 171(1):2-8) postulated that allogeneic blood containing apoptotic lymphocytes may mediate an immune-suppressive effect. While others have shown that SN of RBC units can potentiate LPS-induced pro-inflammatory effects in peripheral blood monocytes, the higher centrifugation speed they employed would have spun out the majority of MPs from the SN (Baumgartner et al., *J Interferon Cytokine Res.* 2009; 29(6):333-338). The findings disclosed herein are the first example of standard RBC units inducing the key regulatory cytokine IL-10 and down-regulating LPS-induced TNF-α production by Mφ (FIG. 3).

Figure 4:
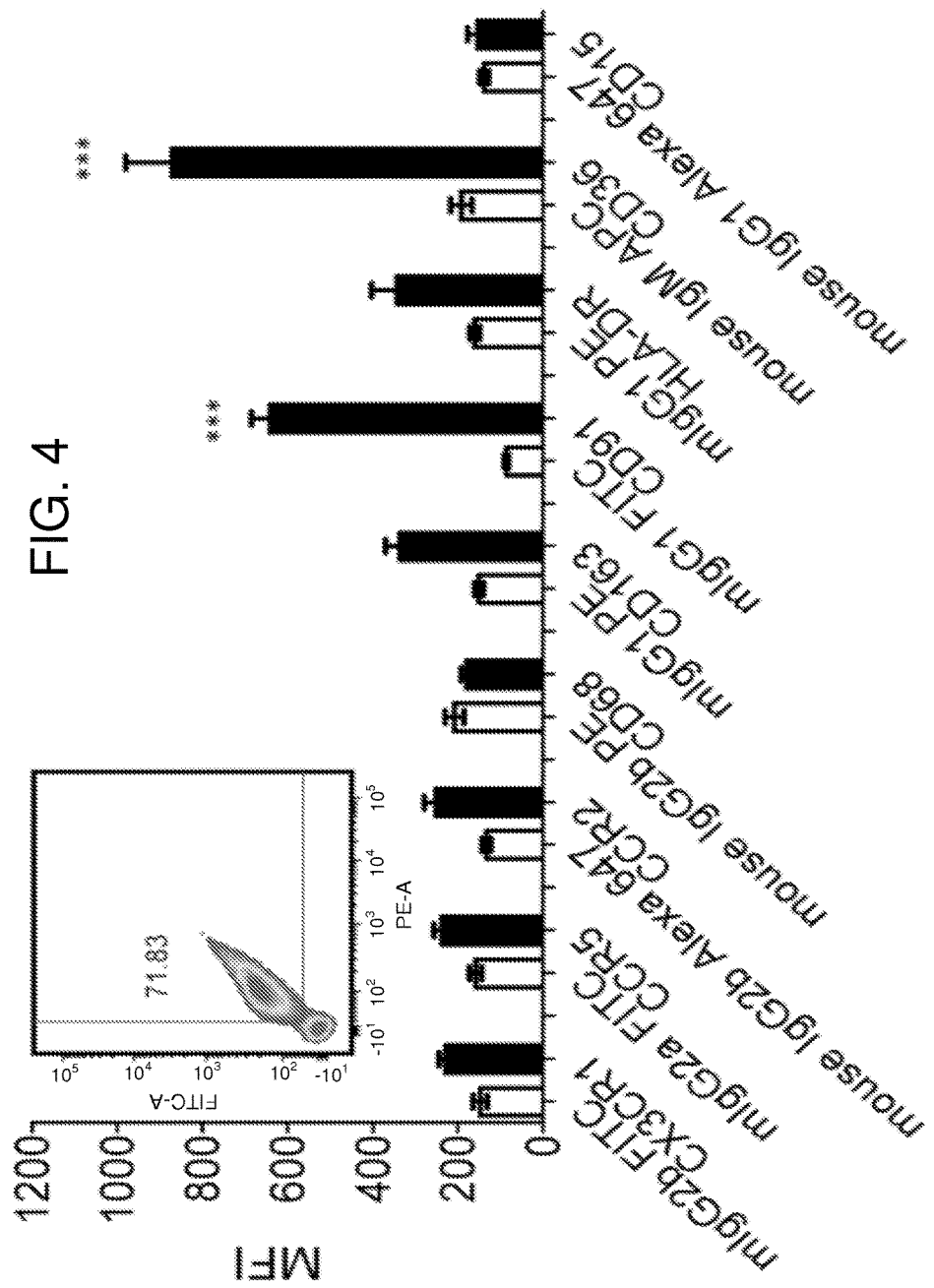
FIG. 4: Human alveolar macrophages show prominent surface expression of the scavenger receptor CD36 and LDL receptor protein 1, CD91. Fiber optic bronchoscopy was performed on healthy volunteers after informed consent. BAL was performed after wedging into the right middle lobe and 200 mL sterile 0.9% NS was introduced in 50 mL aliquots. BAL cell counts and differential was performed and cells were immunostained for various surface receptors or respective control antibodies. A gating strategy involved removal of debris/dead cells and autofluorescent$^{hi}$ population in the FL-1 (FITC) and FL-2 (PE) channels representing macrophages were gated for analysis (see inset). Chemokine receptors (CX3CR1, CCR5, CCR2), scavenger receptors (CD68, CD163, CD91, CD36), HLA-DR and CD15 (a marker for neutrophils—note negative expression) are shown relative to their control antibody immunostaining (white bars). Graph shows relative expression in Mean Fluorescence Intensity (MFI), compiled from n=9 individuals. ***p<0.0001, ANOVA, comparing across all other surface receptors.

Surface Signature of Human Alveolar Macrophages Shows Prominent Scavenger Receptor CD36 and LDL Receptor Protein1 (CD91) Expression While others have shown that liver Kupffer cells are mainly responsible for the removal of oxidatively damaged RBCs from the blood circulation, a process mediated by polyinosinic acid- and PS-sensitive scavenger receptors, the identity of the scavenging receptor(s) that mediate clearance of oxRBC have not been conclusively proven (Terpstra and van Berkel, *Blood.* 2000; 95(6):2157-2163). However, a number of studies suggest CD36 as a candidate molecule. CD36 is required for the recognition of PS on apoptotic cells by human monocyte-derived macrophages (HMDM) (Fadok et al., *J Immunol.* 1998; 161(11):6250-6257) and IL-10 production by macrophages following ingestion of apoptotic cells is, in part, dependent upon CD36 (Chung et al., *Immunity.* 2007; 27(6):952-964). Given the present focus on lung macrophages, the surface signature of human alveolar macrophages from healthy volunteers was examined, which revealed prominent CD36 expression in addition to CD91 (LDL receptor protein 1) also known to bind apoptotic cells (Gardai et al., *Cell.* 2005; 123(2):321-334; Gardai et al., *Cell.* 2003; 115(1):13-23). CD68, a macrophage scavenger receptor found intracellularly (Kurushima et al., *J Leukoc Biol.* 2000; 67(1):104-108; Ramprasad et al., *Proc Natl Acad Sci USA.* 1996; 93(25):14833-14838), shows minimal surface expression in human airspaces even under homeostatic conditions (FIG. 4).

Figure 5C:
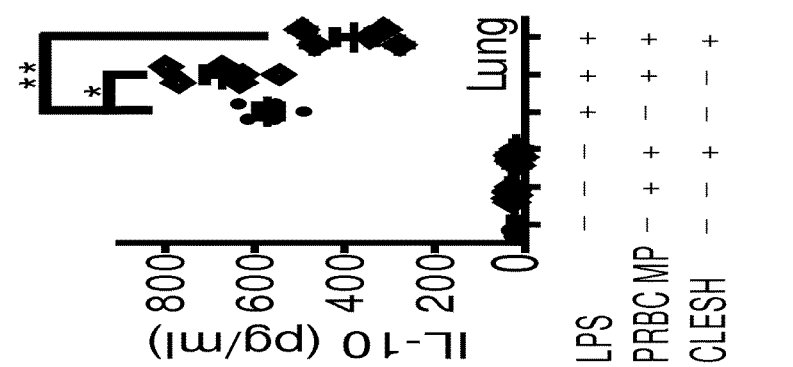
FIGS. 5A-5C: IL-10 responses of human blood and lung tissue mononuclear phagocytes following incubation with constituents of stored RBCs.
Figure 5B:
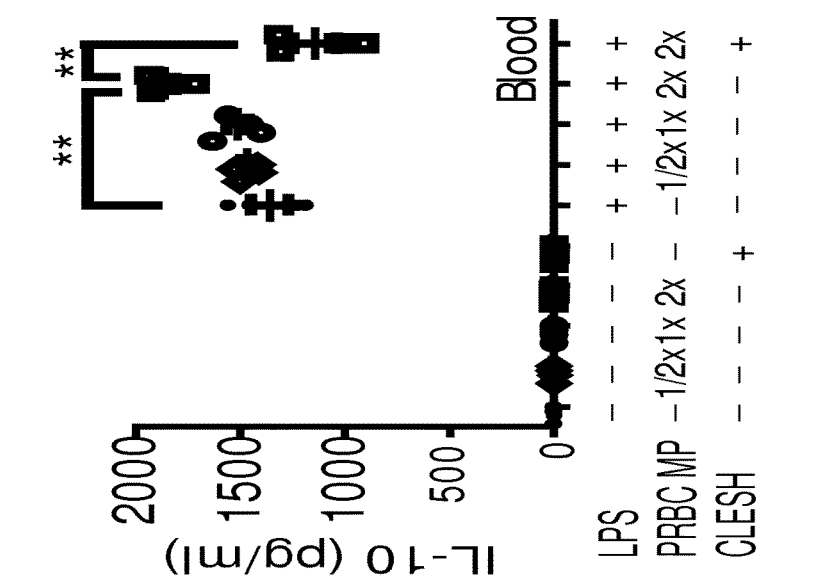
Figure 5A:
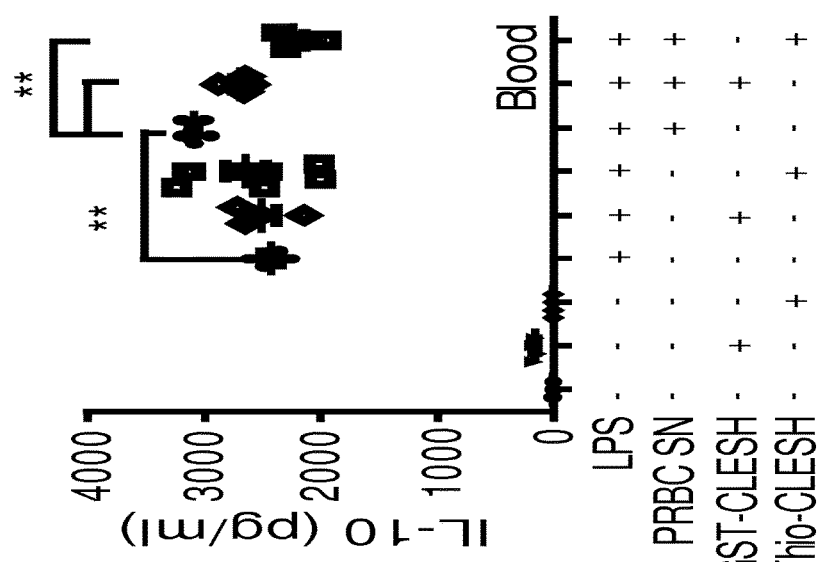

RBC MPs Augment LPS-induced IL-10 Production in Human Blood Monocytes and Lung Tissue Macrophages and Blocking Peptide to Scavenger Receptor CD36 CLESH Domain Inhibits this Response Studies disclosed herein show that RBC MPs isolated from the SN of RBC units can augment IL-10 production in activated human blood monocytes and macrophages isolated from explanted lung tissue through CD14-magnetic bead enrichment (FIG. 5).

Preparations of Ghost RBC MPs Express Surface Phosphatidylserine and RBC Transmembrane Protein Glycophorin A RBC MPs represent membrane-encapsulated Hb, but Hb delivery to macrophages can produce states of iron overload and potential toxicity to macrophages. Therefore, an approach to deplete Hb from MPs was undertaken. In brief, RBCs were purified with the method described by Beutler et al. (*J Lab Clin Med.* 1976; 88(2):328-333). Blood from non-leukoreduced PRBC unit was passed over two Sephadex G25: Microcellulose (1:3; Sigma-Aldrich) columns. The columns were washed 10 times with PBS. This method removes contaminating platelets and leukocytes from blood samples (Xiong et al., *Transfusion.* 2011; 51(3):610-621), and this method provides preparations that are endotoxin-negative (Mangalmurti et al., *Blood.* 2009; 113(5):1158-1166). The eluent was centrifuged at 2000 g for 20 minutes at 4° C. The RBC pellet was washed twice with PBS and then resuspended in hypotonic PBS buffer to lyse cells using the method of Dodge (Dodge et al., *Arch Biochem Biophys.* 1963; 100:119-130). After centrifugation at 20,000 g for 40 minutes, the pellet was washed 3 times with the same hypotonic PBS buffer. Membranes resealed and formed ghost RBC. Storage induced the formation of MPs then can be isolated from the SN, and harvested by ultracentrifugation. The pellet was then resuspended in PBS and protein concentration was determined. FIG. 6 shows the identification, sizing and relative enumeration of human ghost RCB MPs by flow cytometric analysis.

Figure 7A:
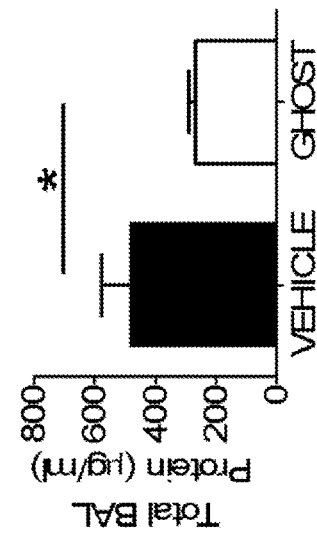
FIGS. 7A-7C: Reduction in markers of inflammation and injury at 6 days post injury in mice receiving ghost RBCs intratracheally. Mice were intratracheally instilled with ghost RBCs prepared from a standard PRBC unit bag. Mice were i.t. challenged with LPS *E. coli* 0111:B4 (3 mg/kg). Twenty-four hours later, mice received either vehicle (100 μL PBS) or ghost RBCs (0.5 mg protein measured/100 μL PBS diluent). Six days post-injury, mice were euthanized and lungs harvested.
Figure 7B:
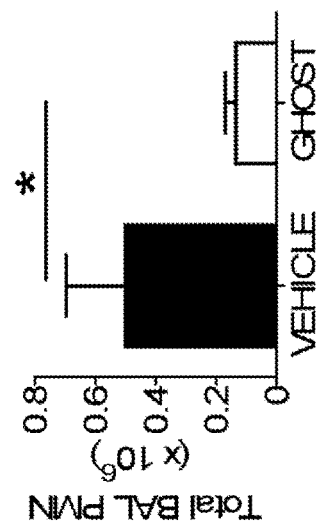
Figure 7C:
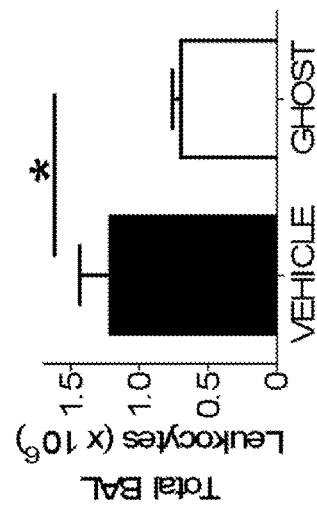

A One-time Intratracheal Administration of Ghost RBCs 24 Hours after LPS-induced Injury in the Lungs Mitigates Inflammation and Lung Leak Mice receiving ghost RBCs 24 hours after injury showed a 42% reduction in total BAL leukocyte counts, 73% reduction in total BAL PMN counts, and 44% reduction in total BAL protein count (marker of lung microvascular permeability) even at 6 days following injury. Instillation of MP therapy after inflammation has occurred and examining days out post-injury more accurately reflects the clinical setting. This study demonstrates in vivo efficacy of utilizing a ghost RBC strategy that can be further optimized by the creation of PSox-enriched ghost MPs for aerosol delivery and dosing (FIG. 7).

RBC MPs can be Efficiently Delivered to the Deep Lung by Nebulization

Figure 8:
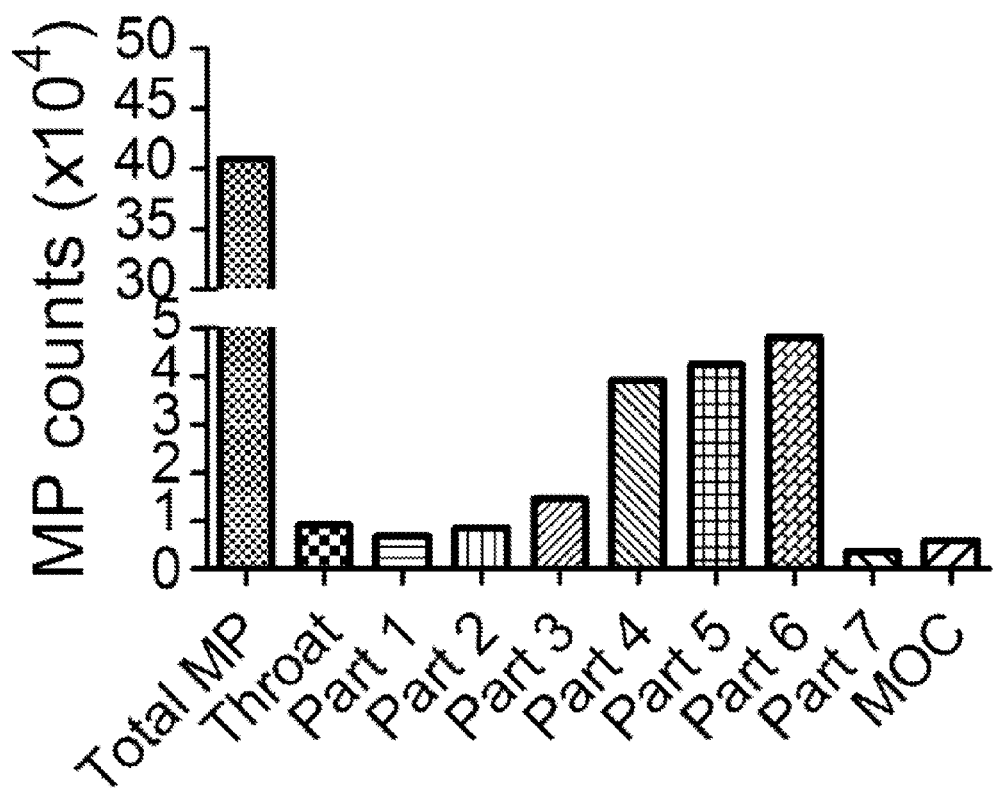
FIG. 8: Aerosolized delivery of RBC MPs by medical nebulizer. The generated aerosol was captured using a USP specified assessment device for inhaled aerosols—the Next Generation Impactor, allowing for the separation of aerosolized droplets based on their size. There is a heavy concentration of AnnexinV$^+$ CD235a$^+$ MPs (MPs) in parts 5 and 6 (based upon relative enumeration by the flow cytometric technique; Xiong et al., *Transfusion*. 2011; 51(3): 610-621) that deposit in the deep lung in humans (and into the murine lung for part 7 and MOC). Very few MPs ended up in the large aerosol size ranges (parts 1-3) that would not penetrate effectively into the lungs. This demonstrates the efficiency of delivering MPs into both human and murine lung using an off the shelf medical nebulizer.

The feasibility of delivering RBC MPs in a liquid aerosol for inhalation was tested using a standard medical nebulizer. The generated aerosol was captured using a USP specified assessment device for inhaled aerosols—the Next Generation Impactor (MSP Corp., Shoreview, Minn.). This device aerodynamically separates and captures aerosol droplets in separate collection stages based on their size. The portion of the aerosol likely to reach and deposit in human alveoli (1.36-3.30 µm) is found in stages 5 and 6 of the device. The portion of the aerosol likely to penetrate beyond the upper airways of the mouse would be captured on stage 7 and the micro-orifice collector (MOC), representing droplets smaller than 1.36 µm. The results indicated substantial delivery of the MPs to the human alveoli and delivery to the murine lung (FIG. 8).

Ghost RBCs can be Labeled with Technetium 99m

Labeling studies of RBC ghosts (from which the MPs will derive) were performed using UltraTag Tc99m RBC labeling kits, which are FDA approved for use in nuclear medicine imaging procedures. A solution containing the ghost RBCs (2 ml) was added to the labeling vial with 0.010 mCi of Tc99m pertechnetate ($TcO_4^-$). After 60 minutes, samples from the vials were spun at 20,000 g for 60 minutes at 4° C. The supernatant was separated from the ghost pellet and radioactivity was measured in both. The pellets were then rehydrated with 0.5 ml of saline and agitated. Paper chromatography with an acetone mobile phase was used to separate unbound $TcO_4^-$ from Tc99m bound to cell fragments in the pellet and supernatant samples in order to determine binding efficiency. An RBC sample was also processed as a control using similar methods. Binding efficiency was high in both the RBC and ghost RBC pellets (99% and 85% respectively). A higher percentage of total radioactivity was found in the supernatant associated with the ghost RBCs compared to the RBCs, but the majority of this radioactivity was bound, likely indicating presence of smaller labeled particles not spun out into the pellet. Overall binding efficiency (% of bound activity in pellet+ % of bound activity in supernatant) was very high in the RBC samples (99%) and moderate in ghost RBCs (60%).

Example 2

Optimization of MP Production from Ghost Biomembranes & Testing of Therapeutic Efficacy and Safety of Delivery in Two Models of Lung Inflammation Hemoglobin (Hb) is the carrier protein for oxygen and provides the essential function of RBCs to deliver oxygen from the lungs to all other organs through the circulation.

However, free Hb released during hemolysis is toxic, and the body possesses protective mechanisms to scavenge and clear plasma free Hb such as plasma haptoglobin. Given the toxic concerns of Hb, the approach described herein is to deplete Hb through the creation of ghost RBCs from which the membrane-derived MPs will derive. The depletion of hemoglobin also removes the theoretical concerns regarding oxidant-mediated injury from free heme, issues with iron overload and concerns regarding the acquisition of non-transferrin bound iron as a pro-survival factor for bacterial pathogens. Studies disclosed herein show ghost RBCs express surface PS and curtail lung inflammation and leak following LPS-induced injury (FIG. 7).

Assessing Effect of Particle Modification Through Depletion of Hb and Inactivation of RBC MPs as Effective Nitric Oxide (NO) Scavengers To assess the purity of ghost MP preps, contaminating Hb is measured by utilizing the Drabkin's method for Hb estimation. As NO scavenging is a highly sensitive functional measurement for free Hb and Hb encased in RBC MPs (Azarov et al., *J Biol Chem.* 2011; 286(38):33567-33579), the ability of ghost MPs (as compared to native RBC MPs) to scavenge NO is measured using routinely used NO consumption assays. MPs (native, containing Hb) and (ghost, depleted of Hb) are assayed in a Sievers NO analyzer where picomoles of NO can be detected (Reiter et al., *Nat Med.* 2002; 8(12):1383-1389). The effect of MPs is assessed by observing the decrease in measured NO as a function of added MPs. In addition, at the end of the reaction the amount of NO scavenged by MPs is assessed by separating MPs and measuring reacted Hb using electron paramagnetic resonance spectroscopy (EPR) according to previously described methods (Azarov et al., *J Biol Chem.* 2005; 280(47):39024-39032). It is believed that ghost MPs fail to consume NO whereas Hb-containing RBC MPs consume NO in a dose-dependent manner.

Assessing the Effect of Ghost MP Aerosol Delivery on Inflammation and Lung Leak in a Sterile LPS-induced Lung Injury Model in Mouse An initial kinetics and dosing study of ghost MPs through an aerosolization approach is performed using a microsprayer aerosolizer (Penn-Century, Inc., or other aerosol cannula technology) that allows for homogenous deposition of MPs into murine lungs. Ghost MPs (0.1, 1, 10 mg/mL), native MPs, or vehicle (PBS) are delivered into the lungs of C57Bl/6 mice 24 hours following i.t. instillation of LPS (3 mg/kg, see FIG. 8). Mice are harvested at 0, 24, 72, 96, 144 hours from the time of LPS instillation and BAL cell counts & differential, BAL total protein, lung tissue and histology obtained. BAL and lung tissues are assayed for TNF-α, IL-6, IL-1β, IL-10, TGF-β1, PGE2, G-CSF and chemokines CXCL½, CXCL5, CCL2. Dosing (0.1, 1, 10 mg/mL) and timing of peak IL-10 responses in the lungs is optimized. In addition to the BAL outcomes mentioned above, lung leak is measured by Evans blue dye extravasation method (Camerer et al., *J Clin Invest.* 2009; 119(7):1871-1879). In select experiments, alveolar macrophages are isolated by magnetic bead separation of CD11c-enriched BAL macrophages and IL-10 ELISPOT is performed for IL-10 production in addition to examining intracellular IL-10 by flow cytometry analysis (Zhao et al., *Mucosal Immunol* 7(2):440-448, 2014).

Assessing Attenuation of Inflammation without Promoting Bacterial Proliferation and Extra-pulmonary Dissemination in a Murine *K. pneumoniae* Model after Aerosol Delivery of Ghost MPs to the Lungs

*K. pneumoniae* strain from ATCC (43816) is used as this strain is well-characterized, shows a robust inflammatory response in mice (Bhan et al., *J Immunol.* 2007; 179(6):3937-3946; Deng et al., *J Immunol.* 2004; 173(8):5148-5155; Deng et al., *J Immunol.* 2004; 173(6):4075-4083; Greenberger et al., *J Immunol.* 1995; 155(2):722-729; Laichalk et al., *Infect Immun.* 1998; 66(6):2822-2826; Laichalk et al., *Infect Immun.* 1996; 64(12):5211-5218), and is a pathogen in humans. Mice are i.t. challenged with *K. pneumoniae* ($10^3$-$10^4$). A standard of absorbances at $OD_{600}$ based upon known CFU are generated to calculate inoculum concentration (Laichalk et al., *Infect Immun.* 1996; 64(12):5211-5218). $OD_{600}$ 0.2-0.25 corresponds to the mid-log phase of growth. The optimal dose of ghost MPs based upon initial studies is used. These studies test whether (1) ghost MPs, native MPs, or vehicle delivered before bacterial challenge in the lungs; or, (2) ghost MPs, native MPs, or vehicle delivered after bacterial challenge in lungs alters neutrophilic inflammation, lung bacterial burden and splenic dissemination. Similar to the data in FIG. 2, others have shown that peak induction of IL-10 in the liver occurred 3-7 days following apoptotic cell administration (Zhang et al., *Hepatology.* 2011; 53(1):306-316). Thus, pre-delivery of ghost MPs is aerosolized several days prior to bacterial challenge. For the post-delivery of ghost MPs, 72 hours is the peak of lung bacterial burden, and thus particles are delivered 24 hours following inoculation to assess its effect at 72 and 96 hours from time of bacterial inoculation. At times 0, 72, and 96 h, lung histology, BAL cell counts and differential, BAL total protein, and cytokine profiles TNF-α, IL-6, IL-10, IL-1β, TGF-β1, PGE2, G-CSF and chemokines CXCL½, CXCL5, CCL2 in BAL and in homogenized lung tissue, are obtained. Quantitative cultures of lung and spleen homogenates are performed as previously published (Lee et al., *Am J Physiol Lung Cell Mol Physiol.* 2005; 289 (5):L731-738; Tan et al., *Am J Respir Cell Mol Biol.* 2006; 34(2):226-232).

Testing Ghost MP Delivery and Impairment of Subsequent Phagocytosis by Human Alveolar Macrophages In Vitro BAL cells are obtained from healthy volunteers by fiberoptic bronchoscopy (as shown in FIG. 4). These cells are counted and allowed to adhere on plastic for 2 hours, and washed gently with warm media containing 10% serum. Alveolar macrophages are then stimulated in vitro with ghost MPs (0, 0.1, 1 mcg/mL) for 60 minutes in the presence or absence of LPS at 37° C., 5% CO2. Cells are gently washed twice and incubated overnight in 10%-20% human AB serum. The following morning, cells are harvested for RNA gene expression profile for cytokines. Another batch of cells (those that received MPs but no LPS) are incubated in the presence or absence of fluorescently labeled heat-killed *E. coli* (K-12 strain) or *S. aureus* (Wood strain, without Protein A) bioparticles (Molecular Probes) (Stone et al., *PLoS Pathog.* 2012; 8 (1):e1002445) in the presence of serum. The fluorescence of bioparticles bound to the surface but not internalized after 60 minutes are quenched with ethidium bromide or trypan blue. Macrophages stimulated with bacterial bioparticles but that did not receive pre-stimulation with ghost MPs serve as the positive control. Negative controls are wells that contain macrophages that are neither stimulated with ghost MP nor bacterial bioparticle. Percent phagocytosis is calculated as net experimental reading/net positive reading×100. Samples are performed in triplicates or quadruplicates depending upon cell numbers obtained from each volunteer. Data are represented as % phagocytosis±SEM, and obtained from at least five different volunteers.

Example 3

Bioengineering the Membrane Surface of RBC MPs to Further Enhance Uptake and Immunoregulatory Function by Macrophages PS represents about 2-10% of lipids constituting the plasma membrane in most eukaryotic cells and is normally sequestered within the inner leaflet of the membrane (Ravichandran and Lorenz, *Nat Rev Immunol.* 2007; 7(12):964-974). Externalized PS on the surface of apoptotic bodies is a signal for phagocyte engulfment, either alone or in combination with other soluble proteins (Ravichandran and Lorenz, *Nat Rev Immunol.* 2007; 7(12):964-974). It is shown herein that creation of RBC expressing externalized PS and its subsequent transfusion induces liver IL-10 production in mice (FIG. 2). As $H_2O_2$ was utilized to oxidize and create these PS-expressing RBC using published methods (Terpstra and van Berkel, *Blood.* 2000; 95(6):2157-2163), it is not known whether the PS in its oxidized form is the necessary signal for IL-10 production on RBC MPs. This has important implications as it is shown that CD36 is a major scavenger receptor expressed on the surface of human alveolar macrophages (FIG. 4) and Greenberg et al. previously showed that oxidized PS interaction with CD36 is essential in macrophage-dependent phagocytosis of apoptotic cells (Greenberg et al., *J Exp Med.* 2006; 203(12):2613-2625). Although a significant percentage of vascular MPs express externalized PS, and surface PS is actually one criteria utilized to define and standardize MPs for clinical studies (Lacroix et al., *Semin Thromb Hemost.* 2010; 36(8):807-818; Lacroix et al., *J Thromb Haemost.* 2010; 8(11):2571-2574; Robert et al., *J Thromb Haemost.* 2009; 7(1):190-197), it is unclear how these circulating particles escape engulfment. A strong possibility is that PS-derived metabolites may differ between endogenous circulating MPs and those derived from stored RBC, the latter of which are formed under oxidative conditions (Wagner et al., *Blood.* 1987; 69(6):1777-1781). As the oxidation state of the PS on microparticles is largely unknown, and prior studies have demonstrated that PS oxidation may influence uptake (Greenberg et al., *J Exp Med.* 2006; 203(12):2613-2625) and quite possibly cytokine production by macrophages, PS is optimized through particle bioengineering. Live cell imaging with confocal microscopy is used to visualize uptake of particles and the effect of particle oxidation on macrophage engulfment.

Methods of measuring and quantifying phosphatidylserine (PS) oxidation are known in the art. For example, Fabisiak et al. (*Methods Mol Biol* 1105:603-611, 2014) describe sensitive and specific assays to measure differential lipid peroxidation in individual phospholipid classes in live cells. The methods described by Fabisiak et al. can readily be applied to evaluating PS oxidation of RBC MPs. In addition, Tyurin et al. (*Cell Death Differ* 21:825-835, 2014) describe linoleic acid (LA) supplementation to increase levels of oxidizable PS molecular species, as well as specific methods to confirm its surface location.

Enriching the RBC MP Membrane in Oxidizable and Oxidized PS

First, the predominant molecular species of PS in stored oxidatively damaged RBC membranes is defined and compared to fresh RBC membranes by LC/ESI-MS analysis by isolating RBC MPs from stored units, as well as creating ghost RBC membranes from stored and fresh RBCs. The molecular species of PS (oxidizable, oxidized, and lyso-PS) are determined and examined for the i) the presence of oxidizable polyunsaturated fatty acid (PUFA)-containing PS species in RBCs; ii) hydroperoxy-, hydroxy-, epoxy-, and oxo-PS species that are the major long-chain oxidation products; in addition there may be oxidatively truncated species of PS. This experiment is designed to specifically define the mol % content of oxidizable and oxidized PS expressed by RBC membranes and whether the damaging conditions of storage induce oxidation of PS species. Should the findings show low oxidizable portion of PS in either membrane preps, stored RBC membranes are manipulated by integrating different amounts of pre-biosynthesized species of PSox (oxidizable stearoyl-linoleoyl-PS (SLPS) or dilinoleoyl-PS (DLPS)) into the RBC membranes. The presence of the oxidizable linoleic acid residue in one (sn2–) position or in both (sn1–/sn2–) positions will provide for the required diversification of PS oxidation products. Following integration with selected oxidizable species of PS, oxidation is undertaken through $H_2O_2$ treatment with subsequent LC/ESI-MS analysis to specifically define and quantify the molecular species of PS and PSox compared to untreated membranes. As Hb can serve as a natural catalyst of PS oxidation, peroxidation of the membrane is initially performed as detailed below prior to the creation of ghost RBCs. Lipids are extracted utilizing the Folch procedure (Folch et al., *J Biol Chem.* 1957; 226(1):497-509) and LC/ESI-MS analysis of PS, PSox and lyso-PS is performed on a Dionex HPLC system (consecutively using normal phase silica column and reverse phase C18 or C8 columns) coupled to a LXQ™ ion trap mass spectrometer with the Xcalibur operating system. Tandem mass spectrometry (MS/MS analysis) is performed to identify PS molecular species (Tyurin et al., *Biochemistry.* 2012; 51(48):9736-9750). Additionally, enzymatically catalyzed peroxidation of PS (using 5- or 12-lipoxygenases or cytochrome c (cyt c)/PS complexes) and subsequent integration of PS into RBC membranes is employed to provide for the desired diversification of PSox molecular species. To this end, oxidizable SLPS or DLPS is treated with lipoxygenases or cytochrome c in the presence of $H_2O_2$ and analyzed by LC/MS (Tyurin et al., *Biochemistry.* 2012; 51(48):9736-9750; Samhan-Arias et al., *Biochim Biophys Acta.* 2012; 1818(10):2413-2423).

Identifying PSox Localization Following $H_2O_2$ Treatment

Following the creation of the PSox-enriched RBC membrane, the RBCs are lysed by exposing the membrane to hypotonic buffer conditions. Following lysis, ghost RBCs (i.e. depleted of Hb) reseal their membranes and the orientation of PS is presumably externally presented as suggested by previous findings (FIG. 6). Phospholipase A2 catalyzes the hydrolysis of phospholipids into fatty acids at the sn-2 acyl position. By using combinations of different phospholipases A2 and subsequent detailed LC-MS analysis of the reaction products—oxidized and non-oxidized lyso-PS as well as oxygenated and non-oxygenated free fatty acids (FFAs)—it is possible to determine the phospholipid species, particularly PS and PSox species, externalized to the surface of ghost RBC membranes. The addition of fatty acid-free BSA (5%) is used in experiments with PLA2. FFA-free BSA effectively binds hydrolysis products (i.e. FFA and lyso-PS) and prevents penetration of phospholipases into cells and protects pools of PS localized in the inner leaflet of plasma membrane from attack. Liberated fatty acids are analyzed by LC/MS using Dionex HPLC system coupled to hybrid quadrupole-orbitrap mass spectrometer, Q-Exactive with the Xcalibur operating system. A reverse phase Luna 3 μm C18 (2) 100 Å column is used for separation of free fatty acids. Employment of lipoprotein-associated phospholipase A2 (Lp-PLA2)—an enzyme with high specificity towards PSox vs PS[63]—is instrumental to the quantitation of PSox species externalized to the RBC membrane surface. Furthermore, as aminophospholipid translocase (APLT) functions to pump PS and phosphatidylethanolamine from the outer to inner plasma membrane monolayer, measurement of APLT is useful to determine whether added PS/PSox remains on the surface versus being internalized. APLT activity is measured using 16:0-12:0 NBD-PS, 1-palmitoyl-2-[12-[(7-nitro-2-1,3-benzoxadiazol-4-yl)amino]dodecanoyl]-sn-glycero-3-phospho-L-serine[65].

Visualizing Uptake of Engineered PSox Enriched Ghost MPs and the Effect of Particle Oxidation on Macrophage Engulfment The ability of Lp-PLA2 to specifically catalyze the hydrolysis of oxidized PS (Tyurin et al., *Biochemistry*. 2012; 51(48):9736-9750) is exploited to examine whether oxidized PS is the predominant determinant of MP engulfment by macrophages. Primary murine peritoneal macrophages are initially utilized as they are relatively easy to obtain by peritoneal lavage 4 days following thioglycollate stimulation (FIG. 3). Later experiments are conducted with murine and human alveolar macrophages to confirm findings (a minimum of three separate experiments each). Engineered ghost RBC MPs enriched for PSox (per 100 μg protein) are incubated with Lp-PLA2 (1, 2.5, 5 μg) at 37° C. for 1 hour. PSox-enriched ghost MPs (herein described as PSox MPs) undergo several wash steps with HBSS, and are labeled with DiI just prior to live cell imaging. PSox MPs (i.e. absence of Lp-PLA2 treatment) are labeled with the lipid membrane dye DiO and serve as controls. It is expected that macrophages will show reduced engulfment of Lp-PLA2 treated PSox MPs, compared with untreated PSox MPs.

To determine the specificity of the Lp-PLA2 effect on macrophage engulfment, MPs are pre-treated with Lp-PLA2 in the presence or absence of Lp-PLA2 specific inhibitor SB435495 (5 microM) (these are labeled with a different lipid membrane dye tracker, DiD). Confirmation of Lp-PLA2 catalyzed hydrolysis and its inhibition is performed by LC/ESI-MS analysis. Live cell imaging of particle engulfment is performed using a Nikon TI inverted microscope equipped with a 60× 1.43-NA oil immersion optic, a Nikon Piezo-driven XYZ stage, a Prairie Sweptfield confocal head, and an Agilent Technologies laser bench (Santa Clara Calif.). Cells are maintained at 37° C. in the microscope with a Tokai Hit environmental stage (Tokyo, Japan). Images are collected using an iXon Ultra (Andor Technology, Belfast). NIS Elements software (Nikon, Melville, N.Y.) is used for both data acquisition and analysis. With respect to image analysis, DiO, DiI, and DiD particles are thresholded and segmented using size and shape appropriate binary masks. Real-time particle accumulation curves are produced by quantification of the emission intensity of the appropriate particles within a defined cytosolic volume (cell tracker blue positive).

Effect of Engineered PSox MPs on Enhancement of Macrophage IL-10 Production

Based upon the findings of LC/ESI-MS analysis of modified particles and macrophage engulfment studies, further studies are performed to determine whether oxidized PS is the predominant determinant of macrophage IL-10 production. As indicated above, engineered PSox MPs are incubated with Lp-PLA2 that selectively hydrolyzes externalized oxidized PS. MPs undergo several wash steps with HBSS, and are incubated with macrophages in the presence or absence of LPS (as shown in FIG. 5). Untreated PSox MPs (i.e. absence of Lp-PLA2 treatment) and standard ghost MPs serve as controls. Macrophages are stimulated overnight and IL-10 production assayed in the SN by ELISA. Although IL-10 is the main read-out in these experiments, the cytokine profile in the SN is examined to assay for TNF-α, IL-6, IL-1β, TGF-β1 and PGE2. To determine the specificity of the Lp-PLA2 effect, Lp-PLA2 treatment is conducted in the presence or absence of Lp-PLA2 specific inhibitor SB435495, followed by assessment of IL-10 production.

Macrophage Cytokine Responses to Engineered PSox MPs Versus PSox Liposomes

If PS alone is sufficient for inducing the anti-inflammatory response, one possibility is to utilize PSox-containing liposomes. Aside from the benefit of CR1 enriched in RBC MPs (Pascual et al., *J Immunol*. 1993; 151(3):1702-1711) and its inhibitory role in complement activation (Iida and Nussenzweig, *J Exp Med*. 1981; 153(5):1138-1150), it is possible that one or more proteins on the RBC MP surface in combination with PS, or PSox optimize recognition by macrophages and alter subsequent immune responses. With this in mind, the effect of PSox-enriched MPs and PSox-enriched liposomes on LPS-treated macrophages is tested. The readouts are the cytokine profile as listed above, with IL-10 as the main determinant. Without limiting the invention, it is believed that macrophages stimulated with PSox-enriched MPs augment IL-10 production and suppress pro-inflammatory cytokines. CD47 expressed by RBC MPs can ligate its putative receptor SIRP-α expressed by macrophages and promote suppressive signals through SHP-1 inhibiting p38 mediated NF-κB activation (Gardai et al., *Cell*. 2003; 115(1):13-23). Although CD47 is a distinct "do not eat-me" signal expressed by virtually all cells, it is possible that the engulfment signals on the engineered MP surface overwhelms the "do not eat me" signal. However, the anti-inflammatory signals transmitted by CD47/SIRP-α may actually strengthen the immunomodulatory effects of RBC MPs. To test this possibility, CD47/SIRP-α interaction is blocked utilizing anti-CD47 blocking antibodies and using cd47−/−RBCs to generate MPs. Cd47−/− mice and blocking antibodies to CD47 are commercially available.

Example 4

Optimization of Techniques for Targeted Delivery of RBC-derived MPs and Other Cell-based Therapies by Inhalation and Developing Novel SPECT/CT Methods for Studying the Kinetics of MPs In Vivo It is believed that specific atomization methods can be developed that will allow cell-based therapies, such as RBC MPs, to be delivered efficiently by aerosol cannula to the murine lung or by inhalation to the human lung without altering their biological activity. It is further believed that Technetium 99m labeling techniques similar to those used clinically to label RBCs can be used to durably label RBC MPs and Micro-SPECT/CT can be used to quantify the kinetics of the MPs providing detailed information on delivery location, post-deposition transport and clearance in mice.

Optimal Methods for Delivering RBC-derived MPs to the Murine Lung Via Aerosol-cannula and the Human Lung Via Inhaled Aerosol Direct instillation is often used to deliver drugs to the murine lung, however it does not provide uniform distribution in the periphery and lacks repeatability and accuracy. The efficiency, accuracy, and repeatability of cell product delivery to the murine lung is optimized using cannulated delivery from existing and novel aerosol technologies. Precise measurements of aerosol size (a key determinant of aerosol penetration), MP delivery rate, and biological activity are performed and then the use of these technologies is translated into murine studies. Available spraying devices (Penn Century MicroSprayer), as well as cannulated delivery of very fine nebulized aerosols generated upstream, are evaluated using methods previously developed for aerosol delivery to infants (Bhashyam et al., *J Aerosol Med Pulm Drug Deliv.* 2008; 21(2):181-188). In order to develop the very small aerosols required for deep lung delivery in murine models, aerosol drying tubes and methods similar to those described by Tian et al. (Tian et al., *J Aerosol Med Pulm Drug Deliv.* 2013) are utilized. These methods dry the liquid aerosol briefly, evaporating water from the droplets and decreasing aerosol size, substantially improving aerosol penetration. The aerosol size is measured using both optical methods (laser diffraction) and by collection using the Next Generation Pharmaceutical Impactor (NGI). This device aerodynamically separates and collects the aerosol into different size classes which can be associated with specific deposition locations in the human lung or penetration ability into the murine lung.

To assess MP content in NGI samples, two different methodologies are employed: (1) Relative enumeration of MPs by flow cytometric analysis coupled with (2) total protein measurements of delivered MPs to quantify the % total dose of MPs delivered by the different aerosol technologies to different lung zones. Biological assays are performed by placing collected aerosol onto cultured macrophages (+/−LPS, 10-100 ng/mL) with IL-10 production as the main indicator of biological activity (although TNF-α, IL-6, IL-1β, TGF-β1 and PGE2 are also measured as described above). In order to facilitate future human use of this and other cell based therapies, a variety of aerosol delivery technologies are tested, including jet, ultrasonic, and micro-pump nebulizers to atomize a liquid aerosol containing human RBC MPs (ghost MPs, or PSox MPs). Precise measurements of aerosol size, microparticle delivery rate, and biological activity are performed using methods similar to those described above. For application in lung transplant, targeting of the aerosols to the small airways and alveoli would improve availability of the MPs to lung macrophages in proximity to the lesions associated with OB. This targeting (essentially an aerosol size specification coupled with an inhalation pattern) is performed using a combination of empirical computer models that have been developed to predict aerosol deposited dose based on detailed characterizations of aerosol size (Corcoran et al., *Am J Transplant.* 2006; 6(11):2765-2773) and measurements performed with the NGI. The final product of this development is an optimized aerosol delivery system for use in future clinical studies of RBC-derived MPs and applicable to the delivery of other cell based therapies by inhalation.

Technetium99m (Tc99m) Labeling Method for RBC-derived MPs for Identifying the Durability of the Label in the Pulmonary Environment There is an extensive history of labeling RBC's with Technetium 99m using FDA approved labeling kits that provide labeling durations of 97% at 24 hours (Mallinckrodt. Package Insert—UltraTag RBC Kit for the preparation of Technetium Tc99m labeled red blood cells. 2012). Similar techniques have previously been used to label lipid complexed antifungal medications for inhaled delivery to lung transplant recipients (Corcoran et al., *Am J Transplant.* 2006; 6(11):2765-2773). Tc99m has a half-life of over 6 hours and mucociliary clearance for up to 24 hours has been imaged using other Tc99m labeled particles. Studies indicate that the RBC labeling kits are effective in labeling ghost RBCs from which the MPs derive. ULTRATAG™ RBC labeling kits are used to label the MPs and verify the label using centrifugation (to separate particles from supernatant), serial filtration techniques are used to assess labeling within specific particle size groups and paper chromatography is used to detect unbound $TcO_4$. Tc99m-MPs are placed onto primary human bronchial epithelial cell cultures for up to 24 hours to verify the durability of the label in the lung environment. The detection of unbound $TcO_4^-$ via paper chromatography in culture washes is indicative of loss of binding.

The kinetics of Tc99m-MP uptake by murine macrophage cultures is examined and unbound vs bound label in the SN is determined. It is expected that the Tc99m label will become progressively associated with macrophages. As receptor-ligand interactions on the cell surface are disrupted at low pH and that internalization is a temperature sensitive process, surface bound versus internalized label is determined by utilizing low-pH wash buffer and/or 4° C. conditions as previously published for examining $I^{125}$-labeled chemokine endocytosis (Zhao et al., *PLoS One.* 2011; 6 (12):e29624). The validity of this low pH wash technique to disrupt surface bound MP is confirmed utilizing DiO-labeled MP and is visualized by live cell imaging. Quality assurance tests are designed to test successive batches of labeled MPs during their use in animal models.

Micro-SPECT/CT of the Delivery and Kinetics of RBC-derived MPs after Delivery to the Murine Lung The aerosol delivery and radiolabeling techniques described above are used to deliver Tc99m labeled MPs to the lungs of mice. Micro-SPECT/CT is used, as this imaging modality allows for the detection of the radioactivity associated with the labeled MP's overlaid onto the anatomical imaging provided by the CT scan, allowing one to locate, track, and quantify radiolabeled MP doses. The total and regional MP doses are determined, including the dose delivered to the peripheral lung. The kinetics of the MPs is also tracked over time. The micro-SPECT/CT system (Siemens Inveon PET/SPECT/CT) is also utilized. The mice are anesthetized using inhalational isoflurane during the study. Technetium 99m labeled MP's are delivered by aerosol cannula. SPECT protocols include the collection of multiple image projections allowing the creation of transverse, sagittal, or coronal views, or 3D reconstructions. Respiratory gating of the images is utilized to minimize the motion artifact associated with normal breathing. Estimated SPECT scan duration is 20-24 minutes.

After SPECT collection, CT imaging is performed. This imaging sequence is repeated at t=30, 60, 90, and 120 minutes. Mice are then removed from the scanner and rehoused. Follow-up scans are performed at t=8 and 24 hours. Axial slices from the t=0 time point are used to determine central and peripheral dose on a percentage basis. A whole lung region of interest (ROI) is assigned based on the CT outline of the lung at each axial level. A rectangular ROI is assigned inside of the whole lung ROI that encompasses the large central airways on each slice. Peripheral dose is calculated as whole lung ROI counts minus airway ROI counts. Lung pixel area is used to weight the contribution of each slice and overall central and peripheral lung dose percentages are calculated. Extra-pulmonary dose is also quantified. Similar procedures are performed using a single coronal view for separate analysis. Kinetics analysis is performed by considering: (1) the change in total decay-corrected lung activity from t=0–120 minutes and 8 and 24 hours using a planar (coronal) view, (2) the change in central vs. peripheral lung activity in a similar view, and (3) the change in central vs. peripheral dose in the entire series of axial images at similar time points. Changes in overall central and peripheral dose percentages are also calculated vs. time using data from assessment 3. Whole-body images are also assessed to determine whether MP activity is concentrating in other parts of the body. GI dosing is expected but other penetration beyond the lung compartment is not. In lung images, two-phase clearance is expected as centrally deposited MPs clear rapidly through mucociliary clearance while peripherally deposited/macrophage associated MPs are retained for substantially longer periods. These techniques form a feasible basis for similar future studies in human subjects. Previous studies have labeled and delivered lipid complexed amphotericin-B using similar labeling and imaging techniques (Corcoran et al., *Am J Transplant.* 2006; 6 (11):2765-2773).

Example 5

Protocols for the Preparation of Ghost RBCs and Subsequent MPs

This example provides two exemplary methods for preparing ghost RBCs.

The method described below is based in part on the method described by Dodge et al. (*Arch Biochem Biophys* 100:119-130, 1963):
1. Pipette 1 ml of washed erythrocytes into centrifuge tube
2. Add 9 ml of cold isotonic buffer (pH 7.4)
3. Store tubes at 4° C. for 30 min
4. Centrifuge at 4000 g for 20 minutes; decant buffer
5. Resuspend cells in 20 ideal milliosmolar buffer (ratio of cells:buffer is 1:15)
6. Use a jet stream of hypotonic buffer from wash bottle to break the button of cells
7. Centrifuge at 20,000 g for 40 minutes at 4° C., decant supernatant
8. Wash 3 more times in hypotonic buffer
9. Resuspend ghost RBCs in PBS in 1-2 mL
10. Storage of ghost RBCs at 4° C. at least 3-5 days to induce formation of MPs
11. Centrifuge at 2,000 g for 20 min at 4° C.
12. Filter SN through sterile 0.8 micron syringe filter
13. Centrifuge SN at 37,000 g for 1 h at 4° C.
14. Resuspend pellet in PBS, and centrifuge again at 37,000 g for 1 h at 4° C.
15. Resuspend pellet in PBS, and keep at 4° C. for protein quantification and flow cytometric analysis, and place aliquot in 2.5% glutaraldehyde for EM Buffers
Sodium phosphate, monobasic (NaH$_2$PO$_4$; FW 137.99) 0.155 M or 310 ideal milliosmolar (21.4 g in 1 L DiH$_2$O)
Sodium phosphate, dibasic (Na$_2$HPO$_4$; FW 141.96) 0.103 M or 310 mOsm (14.63 g in 1 L DiH$_2$O).
Mix the appropriate volumes of the Mono and Disodium buffers to obtain the isotonic buffer @ pH 7.4 @ 25° (room temp.) the day before use. Store in the refrigerator and use cold the next day.
Dilute the Isotonic buffer 1:15 in DiH2O to make the hypotonic buffer.

The method described below, for preparation of ghost RBCs and subsequent MPs, is based in part on the method described by Dodge et al. (*Arch Biochem Biophys* 100:119-130, 1963). The optimal storage duration of ghost RBCs to induce formation of MPs is based in part on the method described by Lutz et al. (*J Biol Chem* 251(11): 3500-3510, 1976):
1. Pipette 10 mL of RBCs from standard issue packed RBCs near to the date of expiry into 50 mL centrifuge tube
2. Centrifuge at 600 g for 10 minutes and decant supernatant
3. Add 10 volumes cold isotonic buffer (pH 7.4) to 1 volume RBC
4. Store tubes at 4° C. for 30 minutes
5. Centrifuge at 4000 g for 20 minutes; decant buffer
6. Resuspend cells in cold hypotonic buffer (ratio of cells:buffer is 1:15)
7. Use a jet stream of hypotonic buffer from wash bottle to break the button of cells
8. Centrifuge at 30,000 g for 30 minutes at 4° C.; use polyallomer ultracentrifuge tubes pretreated with Polymyxin B (60 mg/mL) overnight and washed three times with sterile water to remove LPS from tubes
9. Decant supernatant; wash 3 more times in hypotonic buffer
10. Resuspend ghost RBCs in PBS
11. Storage of ghost RBCs at 4° C. for 48 hours to induce formation of MPs
12. Centrifuge at 2,000 g for 20 minutes at 4° C.
13. Filter SN through sterile 0.8 micron syringe filter
14. Centrifuge SN at 37,000 g for 1 hour at 4° C.
15. Resuspend pellet in PBS, and centrifuge again at 37,000 g for 1 hour at 4° C.
16. Resuspend pellet in PBS, and keep at 4° C. for protein quantification and flow cytometric analysis; place aliquot in 2.5% glutaraldehyde for EM for immediate use, or save aliquots at −80° C. until use.

Buffers
Sodium phosphate, monobasic (NaH$_2$PO$_4$; FW 137.99) 0.155 M or 310 ideal milliosmolar (21.4 g in 1 L DiH$_2$O)
Sodium phosphate, dibasic (Na$_2$HPO$_4$; FW 141.96) 0.103 M or 310 mOsm (14.63 g in 1 L DiH$_2$O).
Preparation of cold isotonic phosphate buffer (pH 7.4): Mix the appropriate volumes of the Mono and Disodium buffers to obtain the isotonic buffer @ pH 7.4 (22.6 volume of 0.155M NaH$_2$PO$_4$, 77.4 volume of 0.103 M Na$_2$HPO$_4$) @ 25° C. the day before use. Store in the refrigerator and use cold the next day.
Preparation of cold hypotonic phosphate buffer (pH 7.4): Dilute the isotonic buffer 1:15 in DiH2O to make hypotonic buffer (yielding sodium phosphate monobasic Na$_2$HPO$_4$ 20 ideal milliosmolar, sodium phosphate dibasic Na$_2$HPO$_4$ 20 ideal milliosmolar).

Example 6

Hb-depleted Ghost MPs Induce IL-10 Production that can be Blocked by CLESH

This example describes testing of ghost MPs in a functional assay, which demonstrated that ghost MPs induce anti-inflammatory responses in human blood monocytes.

Figure 9A:
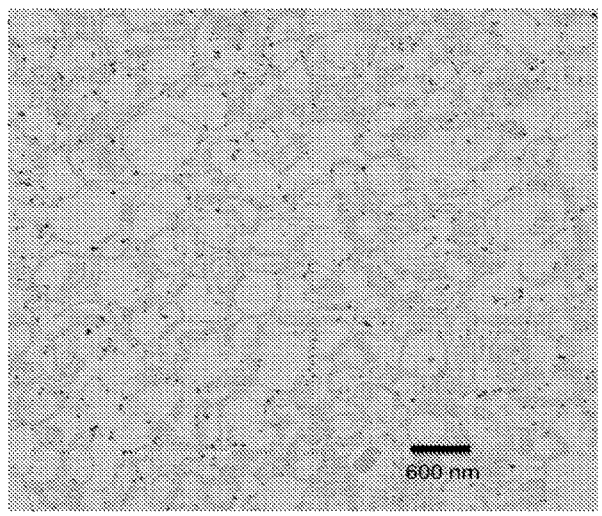
FIGS. 9A-9C: Hb-depleted ghost MPs induce IL-10 production.
Figure 9B:
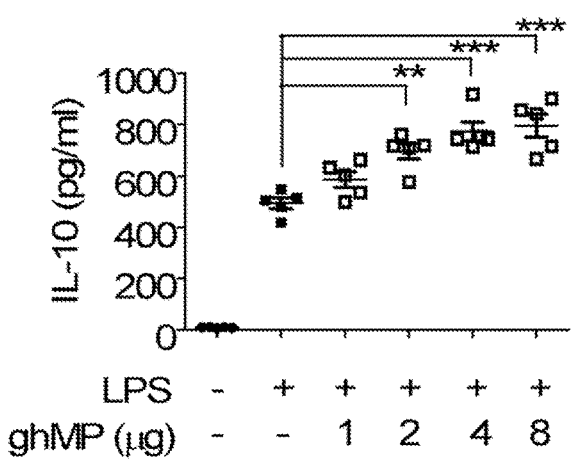
Figure 9C:
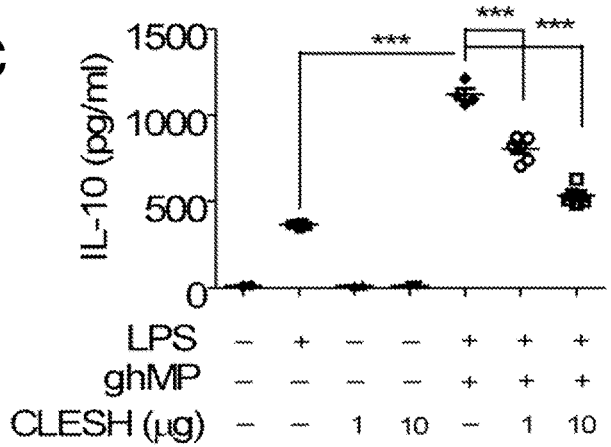

FIG. 9 shows Hb-depleted ghost MPs induce IL-10 production. In particular, FIG. 9A is a transmission electron microscopy image of ghost RBC-derived MPs isolated according to the methods described in Example 5. FIG. 9B is a graph showing that LPS-induced IL-10 production by human PBMCs is enhanced with ghost MPs (ghMP) in a concentration-dependent fashion. To carry out this experiment, ghMPs were originally isolated from stored PRBC units near the date of expiration. Freshly isolated human monocytes were incubated at 37° C. in 5% CO$_2$ for about 2 hours for attachment in a 24-well microtiter plate in complete RPMI-1640 medium with 10% autologous serum. Cells were induced with LPS (10 ng/ml) for 1 hour at 37° C. in 5% CO$_2$. Different concentrations ghMP were added and incubated at the same condition for 18 hours. Supernatants were collected and centrifuged at 13,000 rpm for 5 minutes. A portion (100 µl) of those samples was transferred to 96-well plates and IL-10 was detected by ELISA. All samples were assayed in duplicate. The data shown in FIG. 9B represents combined values from two independent studies using PBMCs from two healthy volunteers. FIG. 9C is a graph showing that LPS-induced IL-10 production by human PBMCs is enhanced with ghMPs. PBMCs were pre-incubated in the absence or presence of CLESH peptide (0, 1 or 10 µg) for 1 hour, then stimulated with LPS (10 ng/mL) for another hour. ghMPs were added to select wells at 4 µg and PBMCs were incubated for 18 hours. Supernatants were collected and assayed for IL-10 as described above. The data shown in FIG. 9C was obtained from separate well conditions using PBMCs from healthy volunteer and is representative of two independent experiments.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. An engineered or artificial red blood cell membrane-derived microparticle (RBC MP) comprising biosynthesized oxidized stearoyl-linoleoyl-phosphatidylserine (SLPS) or dilinoleoyl-phosphatidylserine (DLPS), wherein the SLPS or DLPS is oxidized by treatment with lipoxygenases or cytochrome c on the presence of hydrogen peroxide (H$_2$O$_2$).

2. The engineered or artificial RBC MP of claim 1, wherein the RBC MP is about 100 to about 1000 nm in diameter.

3. The engineered or artificial RBC MP of claim 1, wherein the RBC MP is about 200 to about 300 nm in diameter.

4. The artificial RBC MP of claim 1, wherein the artificial RBC MP comprises an artificial liposome.

5. A composition comprising the engineered or artificial RBC MP of claim 1 and a pharmaceutically acceptable carrier.

6. The composition of claim 5 formulated for administration by inhalation.

7. The composition of claim 6, wherein the composition is formulated as a liquid aerosol for administration by inhalation.

8. The composition of claim 7, wherein the droplet size range of the liquid aerosol is 1-5 µm.

9. The composition of claim 7, wherein the droplet size range of the liquid aerosol is 1.36-3.30 µm.

10. A method, comprising administering to a subject the engineered or artificial red blood cell microparticles (RBC MPs) of claim 1 by inhalation.

11. The method of claim 10, wherein the engineered or artificial RBC MPs are administered as a liquid aerosol for inhalation.

12. The method of claim 10, wherein the engineered or artificial RBC MPs are administered as a dry powder for inhalation.

13. The method of claim 10, wherein the engineered or artificial RBC MPs are administered using a nebulizer, metered dose inhaler or dry powder inhaler.

14. The method of claim 10, wherein the engineered or artificial RBC MPs are about 100 to about 1000 nm in diameter.

15. The method of claim 14, wherein the engineered or artificial RBC MPs are about 200 to about 300 nm in diameter.

* * * * *